(12) United States Patent
Ahmad et al.

(10) Patent No.: US 7,217,693 B2
(45) Date of Patent: May 15, 2007

(54) HUMAN G PROTEIN-COUPLED RECEPTOR EXPRESSED IN THE DORSAL ROOT GANGLIA

(75) Inventors: Sultan Ahmad, St Laurent (CA); Denis Banville, Ste-Dorothee (CA); Yves Fortin, Montreal (CA); Paola Lembo, St Laurent (CA); Dajan O'Donnell, St Laurent (CA); Shi-Hsiang Shen, Beaconsfield (CA)

(73) Assignee: National Research Council of Canada, Ottawa (CA)

( * ) Notice: Subject to any disclaimer, the term of this patent is extended or adjusted under 35 U.S.C. 154(b) by 0 days.

(21) Appl. No.: 10/747,702

(22) Filed: Dec. 30, 2003

(65) Prior Publication Data

US 2006/0068466 A1   Mar. 30, 2006

Related U.S. Application Data

(63) Continuation of application No. 09/254,227, filed as application No. PCT/SE98/02348 on Dec. 16, 1998, now Pat. No. 6,696,257.

(30) Foreign Application Priority Data

Dec. 22, 1997   (SE)   .................................... 9704836

(51) Int. Cl.
*A61K 38/17* (2006.01)
*C07K 14/435* (2006.01)

(52) U.S. Cl. ......................................... 514/12; 530/350
(58) Field of Classification Search .................... None
See application file for complete search history.

(56) References Cited

FOREIGN PATENT DOCUMENTS

| WO | WO 94/05695 | 3/1994 |
|----|-------------|--------|
| WO | WO 95/04073 | 2/1995 |

OTHER PUBLICATIONS

Bowie, et al., "Deciphering the Message in Protein Sequences: Tolerance to Amino Acid Substitutions," *Science* 247:1306-1310 (1990).

Brown, et al., "Gastrointestinal Adaptation to Enhanced Small Intestinal Lipid Exposure," *Gut* 35:1409-1412 (1994).

Caron, et al., "Catecholamine Receptors: Structure, Function, and Regulation," *Rec. Prog. Horm. Res.* 48:277-290 (1993).

Freedman, et al., "Desensitization of G Protein-Coupled Receptors," *Rec. Prog. Horm. Res.* 51:319-353 (1996).

Gudermann, et al., "Receptors and G Proteins as Primary Components of Transmembrane Signal Transduction," *J. Mol. Med.* 73:51-63 (1995).

Mikayama, "Molecular Cloning and Functional Expression of cDNA Encoding Glycosylation-Inhibiting Factor," *Proc. Natl. Acad. Sci. USA* 90:10056-10060 (1993).

Oldfield, et al., "Distribution of Angiotensin II Receptor Binding in the Spinal Cord of the Sheep," *Brain Res.* 650:40-48 (1994)—Dialog abstr., file 154, MEDLINE, Dialog acc. No. 09044093, Medline acc. No. 95041487.

Shapiro, et al., "Angiotensin-II Inhibits Calcium and M-Current Channels in Rat Sympathetic Neurons via G-Proteins," *Neuron* 12:1319-1329 (1994)—Dialog abstr., file 34, SciSearch, Dialog acc. No. 03259572.

Stromberg, et al., Angiotensin II ATI Receptors in Rat Superior Cervical Ganglia Characterization and Stimulation of Phosphoinositide Hydrolysis, *Eur. J. Pharmacol.* 208:331-336 (1991)—Dialog abstr., file 154, MEDLINE, Dialog acc. No. 0692770, Medline acc No. 92275043.

Voet, et al., *Biochemistry*, John Wiley & Sons, Inc., pp. 126-128 and 228-234 (1990).

Handy et al., "Shotgun (sequencing) wedding: can human gene patents and science live happily ever after?" Biotechnology Law Report (2000) 19(6):801-813.

Larhammer et al., "The receptor revolution-multiplicity of G-protein-coupled receptors," Drug Design and Discovery (1993) 9:179-188.

Lembo et al., "Proenkephalin A gene products activate a new family of sensory neuron-specific GBCRs," Nature Neuroscience (2002) 5(3):201-209.

Wilson et al., "Orphan G-protein-coupled receptors: the next generation of drug targets?" British J Pharmacol (1998) 125:1378-1392.

European Offical Communication dated May 8, 2003 for EP Application No. 98964614.6-2405.

*Primary Examiner*—Ruixiang Li
(74) *Attorney, Agent, or Firm*—Robin Quartin; Pepper Hamilton LLP

(57) ABSTRACT

The present invention is directed to novel G protein-coupled receptors that are found predominantly in the dorsal root ganglia. The invention encompasses both the receptor proteins as well as nucleic acids encoding the proteins. In addition, the present invention is directed to methods and compositions which utilize the receptors.

3 Claims, 6 Drawing Sheets

```
         10         20         30         40         50         60         70
    |    |    |    |    |    |    |    |    |    |    |    |    |    |
GACAACAATA TCGATATTAC ATTATGATCG CGAGAAGAGG GGGCAAGGTT AAGGTGCTCA AATATGGTTT  70
GTGTTCTCAG GGACACTACT GGAAGATTTG TGAGCATGGA TCCAACCATC TCATCCCTCA GTACAGAATC 140
TACAACACTG AATAAAACTG GTCATCCCAG TTGCAGGCCA ATCCTCACCC TGTCCTTCCT GGTCCCCATC 210
ATCACCCTGC TTGGATTGGC AGGAAACACC ATTGTACTCT GGCTCTTGGG ATTCCGCATG CGCAGGAAAG 280
CCATCTCAGT CTACGTCCTC AACCTGTCTC TGGCAGACTC CTTCTTCCTC TGCTGCCATT TTATTGACTC 350

360        370        380        390        400        410        420
    |    |    |    |    |    |    |    |    |    |    |    |    |    |
TCTGATGCGG ATCATGAACT TCTATGGCAT CTATGCCCAT AAATTAAGCA AAGAAATCTT AGGCAATGTA 420
GCATTCATTC CCTATATCTC AGGCCTGAGC ATCCTCAGTG CTATCAGCAC GGAGCGCTGC CTGTCTGTAT 490
TGTGGCCAAT CTGGTACCAC TGCCACCGCC CAAGAAACAT GTCAGCTATT ATATGTGTTC TAATCTGGGT 560
TCTGTCCTTT CTCATGGGCA TCCTTGACTG GTTTTTCTCA GGATTCCTGG GTGAGACTCA CCATCATTTG 630
TGGAAAAATG TTGACTTTAT TGTAACTGCA TTTCTGATTT TTTTATTTAT GCTTCTCTTT GGGTCCAGTC 700

710        720        730        740        750        760        770
    |    |    |    |    |    |    |    |    |    |    |    |    |    |
TGGCGCTACT GGTGAGGATC CTCTGTGGTT CCAGACGGAA ACCACTGTCC AGGCTGTACG TTACAATCTC 770
TCTCACAGTG ATGGTCTACC TCATCTGCGG CCTGCCTCTC GGGCTTTACT TGTTCCTGCT ATATTGGTTT 840
GGGATCCATT TACATTATCC CTTTTGTCAC ATTTACCAAG TTACTGTGCT CCTGTCCTGT GTGAACAGCT 910
GGTTCTTAAA AGGGCTCTGG AGGAGACTCC TGAGGAGGAT GAATATACAG ACAGCCATGT TCAGAAACCC 1050

1060       1070       1080       1090       1100       1110       1120
    |    |    |    |    |    |    |    |    |    |    |    |    |    |
ACTGAGATCT CAGAAAGGAG ATGTTGAGAG TCAGTACAAC ACTAACTTAC TCTGCTCTCA GAAATTNCTC 1120
AGTGATTGCA ATGCTTTCAA ATGTTTGTTT TTAA                                       1154
```

FIG. 1

```
         10         20         30         40         50         60         70
    |    |    |    |    |    |    |    |    |    |    |    |    |    |
MVCVLRDTTG RFVSMDPTIS SLSTESTTLN KTGHPSCRPI LTLSFLVPII TLLGLAGNTI VLWLLGFRMR  70
RKAISVYVLN LSLADSFFLC CHFIDSLMRI MNFYGIYAHK LSKEILGNVA FIPYISGLSI LSAISTERCL 140
SVLWPIWYHC HRPRNMSAII CVLIWVLSFL MGILDWFFSG FLGETHHHLW KNVDFIVTAF LIFLFMLLFG 210
SSLALLVRIL CGSRRKPLSR LYVTISLTVM VYLICGLPLG LYLFLLTWFG IHLHYPFCHI YQVTVLLSCV 280
NSSANPIIYF LVGSFRHRKK HRSLKMVLKR ALEETPEEDE YTDSHVQKPT EISERRC              337
```

```
     280            290            300            310
276 L L S C V N S S A N P I Y F L V G S F R H R K K H R S L K M V L K R A L E E T    3B32.PRO
267 L F S T I N S S A N P I Y F F V G S S K K K R F K E S L K V V L T R A F K D E    HUMANMAS.PRO
301 L F L I N S S A N P F I Y F F V G S L K K R L K E S L R V I L Q R A L A D K      HUMANMRG.PRO
266 L F S T I N S S A N P F I Y F F V G S S K K K R F R E S L K V V L T R A F K D E  MOUSEMAS.PRO
266 L F S T I N S S A N P F I Y F F V G S S K K K R F R E S L K V V L T R A F K D E  RATMAS.PRO
278 L C I C L N S S A K P I V Y F L A G R D K S Q R L W E P L R V V F Q R A L R D G  RTA.PRO 320            330
316 P E E D E Y - - - - - - - T D S H V Q K P T E I S E R R C                        3B32.PRO
307 M Q P R R Q - - - - - - - K D N C N T V T V E T V V W                            HUMANMAS.PRO
341 P E V G R I N K K A A G I D P M E Q P H S T Q H V E N L L P R E H R V D V E T W W  HUMANMRG.PRO
306 M Q P R R Q - - - - - - - E G N G N T V S I I E T V V                            MOUSEMAS.PRO
306 M Q P R R Q - - - - - - - E G N G N T V S I I E T V V                            RATMAS.PRO
318 A E P - - G - - - - - - - D A A S S I P N T V I M E M Q C P S G N A S            RTA.PRO 337                                                                                 3B32.PRO
326 W W W W W W W W W                                                                HUMANMAS.PRO
381                                                                                 HUMANMRG.PRO
324                                                                                 MOUSEMAS.PRO
324                                                                                 RATMAS.PRO
343                                                                                 RTA.PRO
```

```
                                                                    250
201  R I L C G S R K M P L T R L Y V T I L L T V L V F L L C G L P F G I L G A L I Y R M H L N L E V L Y   HUMAN36.pro
201  R I L C G S R K M P L T R L Y V T I L L T V L V F L L C G L P F G I L G A L I Y R M H L N L E V L Y   HUMAN18.pro
201  R I L C G S R K T P L T R L Y V T I L L T V L V F L L C G L P F G I Q W A L F S R T H L D W K V L F   HUMAN23.pro
201  R I L C G S R K I P L T R L Y V T I L L T V L V F L L C G L P F G I Q F F L F L W I H V D P E V L F   HUMAN24.pro
201  R I L C G S R K I P L T R L Y V T I L L T V L V F L L C G L P F G I Q F F L F L W I H V D R E V L F   HUMAN7.pro
201  R I L C G S R K M P L T R L Y V T I L L T V L V F L L C G L P F G I Q W A L F S R I H L D W K V L F   HUMAN40.pro 300
251  C H V Y L V C M S L S S L N S S A N P I I Y F F V G S F R Q R Q N R Q N L K L V L Q R A L Q D K P E   HUMAN36.pro
251  C H V H L V S I F L S A L N S S A N P I I Y F F M G S F R Q L Q N P K T L K L V L Q R A L Q D T P E   HUMAN18.pro
251  C H V H L V S I F L S A L N S S A N P I I Y F F V G S F R Q R Q N R Q N L K L V L Q R A L Q D T P E   HUMAN23.pro
251  C H V H L V S I E L S A L N S S A N P I I Y F F V G S L R Q R Q N R Q N L K L V L Q R A L Q D A S E   HUMAN24.pro
251  C H V H L V S I F L S A L N S S A N P I I Y F F V G S F R Q R Q N R Q N L K L V L Q R D L Q D T P E   HUMAN7.pro
251  C H V Y L V C M S L S S L N S S A N P I I Y F F V G S F R Q R Q N R Q N L K L V L Q R A L Q D K P E   HUMAN40.pro 301  V D K G E G Q L P E E S L E L S G R R L G P                                                           HUMAN36.pro
301  V D E G G W W L P Q E T L E L S G S K L E I                                                           HUMAN18.pro
301  V D E G G G G L P E E I L E L S G S R L E Q                                                           HUMAN23.pro
301  V D E G G G W L P Q E T L E L S G S R L E Q                                                           HUMAN24.pro
301  V D E G G G W L P Q E E I L E L S G S K L E Q                                                           HUMAN7.pro
301  V D K G E G Q L P E E S L E L S G S K L G P                                                           HUMAN40.pro
```

FIG. 4B

SEQUENCE LISTING

<160> NUMBER OF SEQ ID NOS: 22

<210> SEQ ID NO 1
<211> LENGTH: 337
<212> TYPE: PRT
<213> ORGANISM: rat

<400> SEQUENCE: 1

```
Met Val Cys Val Leu Arg Asp Thr Thr Gly Arg Phe Val Ser Met Asp
1               5                   10                  15

Pro Thr Ile Ser Ser Leu Ser Thr Glu Ser Thr Thr Leu Asn Lys Thr
            20                  25                  30

Gly His Pro Ser Cys Arg Pro Ile Leu Thr Leu Ser Phe Leu Val Pro
        35                  40                  45

Ile Ile Thr Leu Leu Gly Leu Ala Gly Asn Thr Ile Val Leu Trp Leu
    50                  55                  60

Leu Gly Phe Arg Met Arg Arg Lys Ala Ile Ser Val Tyr Val Leu Asn
65                  70                  75                  80

Leu Ser Leu Ala Asp Ser Phe Phe Leu Cys Cys His Phe Ile Asp Ser
                85                  90                  95

Leu Met Arg Ile Met Asn Phe Tyr Gly Ile Tyr Ala His Lys Leu Ser
                100                 105                 110

Lys Glu Ile Leu Gly Asn Val Ala Phe Ile Pro Tyr Ile Ser Gly Leu
            115                 120                 125

Ser Ile Leu Ser Ala Ile Ser Thr Glu Arg Cys Leu Ser Val Leu Trp
    130                 135                 140

Pro Ile Trp Tyr His Cys His Arg Pro Arg Asn Met Ser Ala Ile Ile
145                 150                 155                 160

Cys Val Leu Ile Trp Val Leu Ser Phe Leu Met Gly Ile Leu Asp Trp
                165                 170                 175

Phe Phe Ser Gly Phe Leu Gly Glu Thr His His His Leu Trp Lys Asn
                180                 185                 190

Val Asp Phe Ile Val Thr Ala Phe Leu Ile Phe Leu Phe Met Leu Leu
            195                 200                 205

Phe Gly Ser Ser Leu Ala Leu Leu Val Arg Ile Leu Cys Gly Ser Arg
    210                 215                 220

Arg Lys Pro Leu Ser Arg Leu Tyr Val Thr Ile Ser Leu Thr Val Met
225                 230                 235                 240

Val Tyr Leu Ile Cys Gly Leu Pro Leu Gly Leu Tyr Leu Phe Leu Leu
                245                 250                 255
```

```
Tyr Trp Phe Gly Ile His Leu His Tyr Pro Phe Cys His Ile Tyr Gln
            260                 265                 270

Val Thr Val Leu Leu Ser Cys Val Asn Ser Ser Ala Asn Pro Ile Ile
            275                 280                 285

Tyr Phe Leu Val Gly Ser Phe Arg His Arg Lys His Arg Ser Leu
            290                 295                 300

Lys Met Val Leu Lys Arg Ala Leu Glu Glu Thr Pro Glu Asp Glu
305                 310                 315                 320

Tyr Thr Asp Ser His Val Gln Lys Pro Thr Glu Ile Ser Glu Arg Arg
            325                 330                 335

Cys

<210> SEQ ID NO 2
<211> LENGTH: 1011
<212> TYPE: DNA
<213> ORGANISM: rat

<400> SEQUENCE: 2
atggtttgtg ttctcaggga cactactgga agatttgtga gcatggatcc aaccatctca    60
tccctcagta cagaatctac aacactgaat aaaactggtc atcccagttg caggccaatc   120
ctcaccctgt ccttcctggt ccccatcatc accctgcttg gattggcagg aaacaccatt   180
gtactctggc tcttgggatt ccgcatgcgc aggaaagcca tctcagtcta cgtcctcaac   240
ctgtctctgg cagactcctt cttcctctgc tgccatttta ttgactctct gatgcggatc   300
atgaacttct atgcatcta tgcccataaa ttaagcaaag aaatcttagg caatgtagca   360
ttcattccct atatctcagg cctgagcatc ctcagtgcta tcagcacgga gcgctgcctg   420
tctgtattgt ggccaatctg gtaccactgc accgcccaa gaaacatgtc agctattata   480
tgtgttctaa tctgggttct gtcctttctc atgggcatcc ttgactggtt tttctcagga   540
ttcctgggtg agactcacca tcatttgtgg aaaaatgttg actttattgt aactgcattt   600
ctgatttttt tatttatgct tctctttggg tccagtctgg cgctactggt gaggatcctc   660
tgtggttcca gacggaaacc actgtccagg ctgtacgtta caatctctct cacagtgatg   720
gtctacctca tctgcggcct gcctctcggg ctttacttgt tcctgctata ttggtttggg   780
atccatttac attatccctt ttgtcacatt taccaagtta ctgtgctcct gtcctgtgtg   840
aacagctctg ccaaccccat catttacttc cttgtagggt cctttaggca ccgtaaaaag   900
catcggtccc tcaaaatggt tcttaaaagg gctctggagg agactcctga ggaggatgaa   960
tatacagaca gccatgttca gaaacccact gagatctcag aaaggagatg t          1011

<210> SEQ ID NO 3
<211> LENGTH: 322
<212> TYPE: PRT
<213> ORGANISM: Homo sapiens

<400> SEQUENCE: 3

Met Asp Pro Thr Ile Pro Val Leu Gly Thr Lys Leu Thr Pro Ile Asn
1               5                   10                  15

Gly Arg Glu Glu Thr Pro Cys Tyr Asn Gln Thr Leu Ser Phe Thr Gly
            20                  25                  30

Leu Thr Cys Ile Ile Ser Leu Val Ala Leu Thr Gly Asn Ala Val Val
            35                  40                  45

Leu Trp Leu Leu Gly Cys Arg Met Arg Arg Asn Ala Val Ser Ile Tyr
        50                  55                  60
```

-continued

```
Ile Leu Asn Leu Val Ala Ala Asn Phe Leu Phe Leu Ser Gly His Ile
 65                  70                  75                  80

Ile Phe Ser Pro Leu Pro Leu Ile Asn Ile Arg His Pro Ile Ser Lys
             85                  90                  95

Ile Leu Ser Pro Val Met Thr Phe Pro Tyr Phe Ile Gly Leu Ser Met
            100                 105                 110

Leu Ser Ala Ile Ser Thr Glu Arg Cys Leu Ser Ile Leu Trp Pro Ile
        115                 120                 125

Trp Tyr His Cys Arg Arg Pro Arg Tyr Leu Ser Ser Val Met Cys Val
    130                 135                 140

Leu Leu Trp Ala Leu Ser Leu Leu Arg Ser Ile Leu Glu Trp Met Phe
145                 150                 155                 160

Cys Asp Phe Leu Phe Ser Gly Ala Asn Ser Val Trp Cys Glu Thr Ser
                165                 170                 175

Asp Phe Ile Thr Ile Ala Trp Leu Val Phe Leu Cys Val Val Leu Cys
            180                 185                 190

Gly Ser Ser Leu Val Leu Leu Val Arg Ile Leu Cys Gly Ser Arg Lys
        195                 200                 205

Met Pro Leu Thr Arg Leu Tyr Val Thr Ile Leu Leu Thr Val Leu Val
    210                 215                 220

Phe Leu Leu Cys Gly Leu Pro Phe Gly Ile Gln Trp Ala Leu Phe Ser
225                 230                 235                 240

Arg Ile His Leu Asp Trp Lys Val Leu Phe Cys His Val His Leu Val
                245                 250                 255

Ser Ile Phe Leu Ser Ala Leu Asn Ser Ser Ala Asn Pro Ile Ile Tyr
            260                 265                 270

Phe Phe Val Gly Ser Phe Arg Gln Arg Gln Asn Arg Gln Asn Leu Lys
        275                 280                 285

Leu Val Leu Gln Arg Ala Leu Gln Asp Thr Pro Glu Val Asp Glu Gly
    290                 295                 300

Gly Gly Trp Leu Pro Gln Glu Thr Leu Glu Leu Ser Gly Ser Lys Leu
305                 310                 315                 320

Glu Gln
```

<210> SEQ ID NO 4
<211> LENGTH: 969
<212> TYPE: DNA
<213> ORGANISM: Homo sapiens

<400> SEQUENCE: 4

```
atggatccaa ccatcccagt cttgggtaca aaactgacac caatcaacgg acgtgaggag    60
actccttgct acaaccaaac cctgagcttc acggggctga cgtgcatcat ttcccttgtc   120
gcgctgacag gaaacgcggt tgtgctctgg ctcctgggct gccgcatgcg caggaacgct   180
gtctccatct acatcctcaa cctggtcgcg gccaacttcc tcttccttag cggccacatt   240
atatttcgc cgttacccct catcaatatc cgccatccca tctccaaaat cctcagtcct   300
gtgatgacct ttcctactt tataggccta agcatgctga cgccatcag caccgagcgc    360
tgcctgtcca tcctgtggcc catctggtac actgccgcc gcccagata cctgtcatcg    420
gtcatgtgtg tcctgctctg ggccctgtcc ctgctgcgga gtatcctgga gtggatgttc   480
tgtgacttcc tgtttagtgg tgctaattct gtttggtgtg aaacgtcaga tttcattaca   540
atcgcgtggc tggttttttt atgtgtggtt ctctgtgggt ccagcctggt cctgctggtc   600
aggattctct gtggatcccg gaagatgccg ctgaccaggc tgtacgtgac catcctcctc   660
```

```
acagtgctgg tcttcctcct ctgtggcctg cccttttggca ttcagtgggc cctgttttcc    720
aggatccacc tggattggaa agtcttattt tgtcatgtgc atctagtttc catttttcctg   780 tccgctctta acagcagtgc caaccccatc atttacttct tcgtgggctc ctttaggcag   840
cgtcaaaata ggcaaaacct gaagctggtt ctccaaaggg ctctgcagga cacgcctgag   900
gtggatgaag gtggagggtg gcttcctcag gaaaccctgg agctgtcggg aagcaaattg   960
gagcagtga                                                           969
```

```
<210> SEQ ID NO 5
<211> LENGTH: 322
<212> TYPE: PRT
<213> ORGANISM: Homo sapiens

<400> SEQUENCE: 5
```

| Met | Asp | Pro | Thr | Val | Pro | Val | Leu | Gly | Thr | Glu | Leu | Thr | Pro | Ile | Asn |
|-----|-----|-----|-----|-----|-----|-----|-----|-----|-----|-----|-----|-----|-----|-----|-----|
| 1 | | | | 5 | | | | | 10 | | | | | 15 | |

| Gly | Arg | Glu | Glu | Thr | Pro | Cys | Tyr | Lys | Gln | Thr | Leu | Ser | Phe | Thr | Gly |
| | | | 20 | | | | | 25 | | | | | 30 | | |

| Leu | Thr | Cys | Ile | Val | Ser | Leu | Val | Ala | Leu | Thr | Gly | Asn | Ala | Val | Val |
| | | 35 | | | | | 40 | | | | | 45 | | | |

| Leu | Trp | Leu | Leu | Gly | Cys | Arg | Met | Arg | Arg | Asn | Ala | Val | Ser | Ile | Tyr |
| 50 | | | | | 55 | | | | | 60 | | | | | |

| Ile | Leu | Asn | Leu | Val | Ala | Ala | Asp | Phe | Leu | Phe | Leu | Ser | Gly | His | Ile |
| 65 | | | | | 70 | | | | | 75 | | | | | 80 |

| Ile | Cys | Ser | Pro | Leu | Arg | Leu | Ile | Asn | Ile | Ser | His | Pro | Ile | Ser | Lys |
| | | | | 85 | | | | | 90 | | | | | 95 | |

| Ile | Leu | Ser | Pro | Val | Met | Thr | Phe | Pro | Tyr | Phe | Ile | Gly | Leu | Ser | Met |
| | | | | 100 | | | | | 105 | | | | | 110 | |

| Leu | Asn | Ala | Ile | Ser | Thr | Glu | Arg | Cys | Leu | Ser | Ile | Leu | Trp | Pro | Ile |
| | | | 115 | | | | | 120 | | | | | 125 | | |

| Trp | Tyr | His | Cys | Arg | Arg | Pro | Arg | Tyr | Leu | Ser | Ser | Val | Met | Cys | Val |
| | 130 | | | | | 135 | | | | | 140 | | | | |

| Leu | Leu | Trp | Ala | Pro | Ser | Leu | Leu | Arg | Ser | Ile | Leu | Glu | Trp | Met | Phe |
| 145 | | | | | 150 | | | | | 155 | | | | | 160 |

| Cys | Asp | Phe | Leu | Phe | Ser | Gly | Ala | Asp | Ser | Val | Arg | Cys | Glu | Thr | Ser |
| | | | | 165 | | | | | 170 | | | | | 175 | |

| Asp | Phe | Ile | Thr | Ile | Ala | Trp | Leu | Val | Phe | Leu | Arg | Val | Val | Leu | Cys |
| | | | 180 | | | | | 185 | | | | | 190 | | |

| Gly | Ser | Ser | Leu | Val | Leu | Leu | Val | Arg | Ile | Leu | Cys | Gly | Ser | Arg | Lys |
| | | 195 | | | | | 200 | | | | | 205 | | | |

| Met | Pro | Leu | Thr | Arg | Leu | Tyr | Val | Thr | Ile | Leu | Leu | Thr | Val | Leu | Val |
| | 210 | | | | | 215 | | | | | 220 | | | | |

| Phe | Leu | Leu | Cys | Gly | Leu | Pro | Phe | Gly | Ile | Gln | Trp | Ala | Leu | Phe | Ser |
| 225 | | | | | 230 | | | | | 235 | | | | | 240 |

| Arg | Ile | His | Leu | Asp | Trp | Lys | Val | Leu | Phe | Cys | His | Val | His | Leu | Val |
| | | | | 245 | | | | | 250 | | | | | 255 | |

| Ser | Ile | Phe | Leu | Ser | Ala | Leu | Asn | Ser | Ser | Ala | Asn | Pro | Ile | Ile | Tyr |
| | | | 260 | | | | | 265 | | | | | 270 | | |

| Phe | Phe | Met | Gly | Ser | Phe | Arg | Gln | Leu | Gln | Asn | Arg | Lys | Thr | Leu | Lys |
| | | | 275 | | | | | 280 | | | | | 285 | | |

| Leu | Val | Leu | Gln | Arg | Asp | Leu | Gln | Asp | Thr | Pro | Glu | Val | Asp | Glu | Gly |
| | 290 | | | | | 295 | | | | | 300 | | | | |

| Gly | Trp | Trp | Leu | Pro | Gln | Glu | Thr | Leu | Glu | Leu | Ser | Gly | Ser | Lys | Leu |

```
305              310              315              320
Glu Ile

<210> SEQ ID NO 6
<211> LENGTH: 969
<212> TYPE: DNA
<213> ORGANISM: Homo sapiens

<400> SEQUENCE: 6
atggatccaa ccgtcccagt cttgggtaca gaactgacac caatcaacgg acgtgaggag     60
actccttgct acaagcagac cctgagcttc acggggctga cgtgcatcgt ttcccttgtc    120
gcgctgacag gaaacgcggt tgtgctctgg ctcctgggct gccgcatgcg caggaacgct    180
gtctccatct acatcctcaa cctggtcgcg gccgacttcc tcttccttag cggccacatt    240
atatgttcgc cgttacgcct catcaatatc agccatccca tctccaaaat cctcagtcct    300
gtgatgacct ttccctactt tataggccta agcatgctga acgccatcag caccgagcgc    360
tgcctgtcca tcctgtggcc catctggtac cactgccgcc gccccagata cctgtcatcg    420
gtcatgtgtg tcctgctctg ggccccgtcc ctgctgcgga gtatcctgga gtggatgttc    480
tgtgacttcc tgtttagtgg tgctgattct gttcggtgtg aaacgtcaga tttcattaca    540
atcgcgtggc tggttttttt acgtgtggtt ctctgtgggt ccagcctggt cctgctggtc    600
aggattctct gtggatcccg gaagatgccg ctgaccaggc tgtacgtgac catcctcctc    660
acagtgctgg tcttcctcct ctgtggcctg ccctttggca ttcagtgggc cctgttttcc    720
aggatccacc tggattggaa agtcttattt tgtcatgtgc atctagtttc cattttcctg    780
tccgctctta acagcagtgc caaccccatc atttacttct tcatgggctc ctttaggcag    840
cttcaaaaca ggaagaccct caagctggtt ctccagaggg atctgcagga cacgcctgag    900
gtggatgaag tggatggtg gcttcctcag gaaaccctgg agctgtcggg aagcaaattg    960
gagatctga                                                            969

<210> SEQ ID NO 7
<211> LENGTH: 322
<212> TYPE: PRT
<213> ORGANISM: Homo sapiens

<400> SEQUENCE: 7

Met Asp Pro Thr Val Ser Thr Leu Asp Thr Glu Leu Thr Pro Ile Asn
1               5                  10                  15
Gly Thr Glu Glu Thr Leu Cys Tyr Lys Gln Thr Leu Ser Leu Thr Val
                20                  25                  30
Leu Thr Cys Ile Val Ser Leu Val Gly Leu Thr Gly Asn Ala Val Val
            35                  40                  45
Leu Trp Leu Leu Gly Cys Arg Met Arg Arg Asn Ala Phe Ser Ile Tyr
        50                  55                  60
Ile Leu Asn Leu Ala Ala Ala Asp Phe Leu Phe Leu Ser Gly Arg Leu
65                  70                  75                  80
Ile Tyr Ser Leu Leu Ser Phe Ile Ser Ile Pro His Thr Ile Ser Lys
                85                  90                  95
Ile Leu Tyr Pro Val Met Met Phe Ser Tyr Phe Ala Gly Leu Asn Phe
            100                 105                 110
Leu Ser Ala Val Ser Thr Asp Arg Cys Leu Ser Val Leu Trp Pro Ile
        115                 120                 125
Trp Tyr Arg Cys His Arg Pro Thr His Leu Ser Ala Val Val Cys Val
```

```
              130                 135                 140
Leu Leu Trp Ala Leu Ser Leu Leu Arg Ser Ile Leu Glu Trp Met Leu
145                 150                 155                 160

Cys Gly Phe Leu Phe Ser Gly Ala Asp Ser Ala Trp Cys Gln Thr Ser
            165                 170                 175

Asp Phe Ile Thr Val Ala Trp Leu Ile Phe Leu Cys Val Val Leu Cys
                180                 185                 190

Gly Ser Ser Leu Val Leu Leu Ile Arg Ile Leu Cys Gly Ser Arg Lys
            195                 200                 205

Ile Pro Leu Thr Arg Leu Tyr Val Thr Ile Leu Leu Thr Val Leu Val
210                 215                 220

Phe Leu Leu Cys Gly Leu Pro Phe Gly Ile Gln Phe Phe Leu Phe Leu
225                 230                 235                 240

Trp Ile His Val Asp Arg Glu Val Leu Phe Cys His Val His Leu Val
                245                 250                 255

Ser Ile Phe Leu Ser Ala Leu Asn Ser Ser Ala Asn Pro Ile Ile Tyr
                260                 265                 270

Phe Phe Val Gly Ser Leu Arg Gln Arg Gln Asn Arg Gln Asn Leu Lys
            275                 280                 285

Leu Val Leu Gln Arg Ala Leu Gln Asp Thr Pro Glu Val Asp Glu Gly
            290                 295                 300

Gly Gly Trp Leu Pro Gln Glu Thr Leu Glu Leu Ser Gly Ser Arg Leu
305                 310                 315                 320

Glu Gln

<210> SEQ ID NO 8
<211> LENGTH: 969
<212> TYPE: DNA
<213> ORGANISM: Homo sapiens

<400> SEQUENCE: 8
atggatccaa ccgtctcaac cttggacaca gaactgacac caatcaacgg aactgaggag    60
actctttgct acaagcagac cttgagcctc acggtgctga cgtgcatcgt ttcccttgtc   120
gggctgacag gaaacgcagt tgtactctgg ctcctgggct gccgcatgcg caggaacgcc   180
ttctccatct acatcctcaa cttggccgca gcagacttcc tcttcctcag cggccgcctt   240
atatattccc tgttaagctt catcagtatc ccccatacca tctctaaaat cctctatcct   300
gtgatgatgt ttcctacttt gcaggcctg aactttctga gtccgtgag caccgatcgc   360 tgcctgtccg tcctgtggcc catctggtac cgctgccacc gcccacaca cctgtcagcg   420 gtggtgtgtg tcctgctctg ggccctgtcc ctgctgcgga gcatcctgga atggatgtta   480
tgtggcttcc tgttcagtgg tgctgattct gcttggtgtc aaacatcaga tttcatcaca   540
gtcgcgtggc tgatttttt atgtgtggtt ctctgtgggt ccagcctggt cctgctgatc   600
aggattctct gtggatcccg gaagataccg ctgaccaggc tgtacgtgac catcctgctc   660
acagtactgg tcttcctcct ctgtggcctg cccttttggca ttcagttttt cctattttta   720
tggatccacg tggacaggga agtcttattt tgtcatgtgc atctagtttc cattttcctg   780
tccgctctta acagcagtgc caaccccatc atttacttct cgtgggctc ccttaggcag   840 cgtcaaaata ggcagaacct gaagctggtt ctccagaggg ctctgcagga cacgcctgag   900
gtggatgaag tggagggtg gcttcctcag gaaaccctgg agctgtcggg aagcagattg   960
gagcagtga                                                           969
```

<210> SEQ ID NO 9
<211> LENGTH: 322
<212> TYPE: PRT
<213> ORGANISM: Homo sapiens

<400> SEQUENCE: 9

```
Met Asp Pro Thr Val Ser Thr Leu Asp Thr Glu Leu Thr Pro Ile Asn
1               5                   10                  15

Gly Thr Glu Glu Thr Leu Cys Tyr Lys Gln Thr Leu Ser Leu Thr Val
            20                  25                  30

Leu Thr Cys Ile Val Ser Leu Val Gly Leu Thr Gly Asn Ala Val Val
        35                  40                  45

Leu Trp Leu Leu Gly Cys Arg Met Arg Arg Asn Ala Phe Ser Ile Tyr
    50                  55                  60

Ile Leu Asn Leu Ala Ala Ala Asp Phe Leu Phe Leu Ser Gly Arg Leu
65                  70                  75                  80

Ile Tyr Ser Leu Leu Ser Phe Ile Ser Ile Pro His Thr Ile Ser Lys
                85                  90                  95

Ile Leu Tyr Pro Val Met Met Phe Ser Tyr Phe Ala Gly Leu Ser Phe
            100                 105                 110

Leu Ser Ala Val Ser Thr Glu Arg Cys Leu Ser Val Leu Trp Pro Ile
        115                 120                 125

Trp Tyr Arg Cys His Arg Pro Thr His Leu Ser Ala Val Val Cys Val
    130                 135                 140

Leu Leu Trp Ala Leu Ser Leu Leu Arg Ser Ile Leu Glu Trp Met Leu
145                 150                 155                 160

Cys Gly Phe Leu Phe Ser Gly Ala Asp Ser Ala Trp Cys Gln Thr Ser
                165                 170                 175

Asp Phe Ile Thr Val Ala Trp Leu Ile Phe Leu Cys Val Val Leu Cys
            180                 185                 190

Gly Ser Ser Leu Val Leu Leu Ile Arg Ile Leu Cys Gly Ser Arg Lys
        195                 200                 205

Ile Pro Leu Thr Arg Leu Tyr Val Thr Ile Leu Leu Thr Val Leu Val
    210                 215                 220

Phe Leu Leu Cys Gly Leu Pro Phe Gly Ile Gln Phe Phe Leu Phe Leu
225                 230                 235                 240

Trp Ile His Val Asp Arg Glu Val Leu Phe Cys His Val His Leu Val
                245                 250                 255

Ser Ile Phe Leu Ser Ala Leu Asn Ser Ser Ala Asn Pro Ile Ile Tyr
            260                 265                 270

Phe Phe Val Gly Ser Phe Arg Gln Arg Gln Asn Arg Gln Asn Leu Lys
        275                 280                 285

Leu Val Leu Gln Arg Ala Leu Gln Asp Ala Ser Glu Val Asp Glu Gly
    290                 295                 300

Gly Gly Gln Leu Pro Gln Glu Thr Leu Glu Leu Ser Gly Ser Arg Leu
305                 310                 315                 320

Glu Gln
```

<210> SEQ ID NO 10
<211> LENGTH: 969
<212> TYPE: DNA
<213> ORGANISM: Homo sapiens

<400> SEQUENCE: 10
atggatccaa cggtctcaac cttggacaca gaattgacac caatcaacgg aactgaggag    60

-continued

```
actctttgct acaagcagac cttgagcctc acggtgctga cgtgcatcgt ttcccttgtc      120
gggctgacag gaaacgcggt tgtgctctgg ctcctgggct gccgcatgcg caggaacgcc      180
ttctccatct acatcctcaa cttggccgca gcagacttcc tcttcctcag cggccgcctt      240
atatattccc tgttaagctt catcagtatc ccccatacca tctctaaaat cctctatcct      300
gtgatgatgt tttcctactt tgcaggcctg agctttctga gtgccgtgag caccgagcgc      360
tgcctgtccg tcctgtggcc catctggtac cgctgccacc gccccacaca cctgtcagcg      420
gtggtgtgtg tcctgctctg ggccctgtcc ctgctgcgga gcatcctgga gtggatgtta      480
tgtggcttcc tgttcagtgg tgctgattct gcttggtgtc aaacatcaga tttcatcaca      540
gtcgcgtggc tgattttttt atgtgtggtt ctctgtgggt ccagcctggt cctgctgatc      600
aggattctct gtggatcccg gaagataccg ctgaccaggc tgtacgtgac catcctgctc      660
acagtactgg tcttcctcct ctgtggcctg ccctttggca ttcagttttt cctatttta       720 tggatccacg tggacaggga agtcttattt tgtcatgttc atctagtttc tattttcctg      780
tccgctctta acagcagtgc caaccccatc atttacttct cgtgggctc ctttaggcag       840 cgtcaaaata ggcagaacct gaagctggtt ctccagaggg ctctgcagga cgcgtctgag      900
gtggatgaag gtggagggca gcttcctgag gaaatcctgg agctgtcggg aagcagattg      960
gagcagtga                                                             969
```

<210> SEQ ID NO 11
<211> LENGTH: 322
<212> TYPE: PRT
<213> ORGANISM: Homo sapiens

<400> SEQUENCE: 11

```
Met Asp Pro Thr Val Pro Val Leu Gly Thr Lys Leu Thr Pro Ile Asn
1               5                   10                  15

Gly Arg Glu Glu Thr Pro Cys Tyr Lys Gln Thr Leu Ser Phe Thr Val
            20                  25                  30

Leu Thr Cys Ile Ile Ser Leu Val Gly Leu Thr Gly Asn Ala Val Val
        35                  40                  45

Leu Trp Leu Leu Gly Cys Arg Met Arg Arg Asn Ala Val Ser Ile Tyr
    50                  55                  60

Ile Leu Asn Leu Ala Ala Ala Asp Phe Leu Phe Leu Ser Phe Gln Ile
65                  70                  75                  80

Ile Cys Arg Pro Leu Arg Leu Ile Asn Ile Ser His Leu Ile Arg Lys
                85                  90                  95

Ile Leu Val Ser Val Met Thr Phe Pro Tyr Phe Thr Gly Leu Ser Met
            100                 105                 110

Leu Ser Ala Ile Ser Thr Glu Arg Cys Leu Ser Val Leu Trp Pro Ile
        115                 120                 125

Trp Tyr Arg Cys Arg Arg Pro Thr His Leu Ser Ala Val Val Cys Val
    130                 135                 140

Leu Leu Trp Ala Gly Leu Leu Leu Phe Ser Met Leu Glu Trp Arg Phe
145                 150                 155                 160

Cys Asp Phe Leu Phe Ser Gly Ala Asp Ser Ser Trp Cys Glu Thr Ser
                165                 170                 175

Asp Phe Ile Pro Val Ala Trp Leu Ile Phe Leu Cys Val Val Leu Cys
            180                 185                 190

Val Ser Ser Leu Val Leu Leu Val Arg Ile Leu Cys Gly Ser Arg Lys
        195                 200                 205
```

```
Met Pro Leu Thr Arg Leu Tyr Val Thr Ile Leu Leu Thr Val Leu Val
    210                 215                 220

Phe Leu Leu Cys Gly Leu Pro Phe Gly Ile Leu Gly Ala Leu Ile Tyr
225                 230                 235                 240

Arg Met His Leu Asn Leu Glu Val Leu Tyr Cys His Val Tyr Leu Val
                245                 250                 255

Cys Met Ser Leu Ser Ser Leu Asn Ser Ser Ala Asn Pro Ile Ile Tyr
            260                 265                 270

Phe Phe Val Gly Ser Phe Arg Gln Arg Gln Asn Arg Gln Asn Leu Lys
        275                 280                 285

Leu Val Leu Gln Arg Ala Leu Gln Asp Lys Pro Glu Val Asp Lys Gly
    290                 295                 300

Glu Gly Gln Leu Pro Glu Ser Leu Glu Leu Ser Gly Arg Arg Leu
305                 310                 315                 320

Gly Pro

<210> SEQ ID NO 12
<211> LENGTH: 969
<212> TYPE: DNA
<213> ORGANISM: Homo sapiens

<400> SEQUENCE: 12
atggatccaa ccgtcccagt cttgggtaca aaactgacac caatcaacgg acgtgaggag      60
actccttgct acaagcagac cctgagcttc acggtgctga cgtgcatcat ttcccttgtc     120
ggactgacag gaaacgcggt tgtgctctgg ctcctgggct gccgcatgcg caggaacgct     180
gtctccatct acatcctcaa cctggccgca gcagacttcc tcttcctcag cttccaaatt     240
atacgttcgc cattacgcct catcaatatc agccatctca tccgcaaaat cctcgtttct     300
gtgatgacct ttccctactt tacaggcctg agtatgctga cgccatcag caccgagcgc      360 tgcctgtctg ttctgtggcc catctggtac cgctgccgcc gccccacaca cctgtcagcg     420
gtcgtgtgtg tcctgctctg gggcctgtcc ctgctgttta gtatgctgga gtggaggttc     480
tgtgacttcc tgtttagtgg tgctgattct agttggtgtg aaacgtcaga tttcatccca     540
gtcgcgtggc tgattttttt atgtgtggtt ctctgtgttt ccagcctggt cctgctggtc     600
aggatcctct gtggatcccg gaagatgccg ctgaccaggc tgtatgtgac catcctgctc     660
acagtgctgg tcttcctcct ctgcggcctg cccttcggca ttctgggggc cctaatttac     720
aggatgcacc tgaatttgga agtcttatat tgtcatgttt atctggtttg catgtccctg     780
tcctctctaa acagtagtgc caaccccatc atttacttct cgtgggctc ctttaggcag      840 cgtcaaaata ggcagaacct gaagctggtt ctccagaggg ctctgcagga caagcctgag     900
gtggataaag gtgaagggca gcttcctgag gaaagcctgg agctgtcggg aaggagattg     960
gggccatga                                                              969

<210> SEQ ID NO 13
<211> LENGTH: 322
<212> TYPE: PRT
<213> ORGANISM: Homo sapiens

<400> SEQUENCE: 13

Met Asp Pro Thr Val Pro Val Phe Gly Thr Lys Leu Thr Pro Ile Asn
1               5                   10                  15

Gly Arg Glu Glu Thr Pro Cys Tyr Asn Gln Thr Leu Ser Phe Thr Val
            20                  25                  30
```

```
Leu Thr Cys Ile Ile Ser Leu Val Gly Leu Thr Gly Asn Ala Val Val
         35                  40                  45

Leu Trp Leu Leu Gly Tyr Arg Met Arg Arg Asn Ala Val Ser Ile Tyr
 50                  55                  60

Ile Leu Asn Leu Ala Ala Ala Asp Phe Leu Phe Leu Ser Phe Gln Ile
65                  70                  75                  80

Ile Arg Ser Pro Leu Arg Leu Ile Asn Ile Ser His Leu Ile Arg Lys
                 85                  90                  95

Ile Leu Val Ser Val Met Thr Phe Pro Tyr Phe Thr Gly Leu Ser Met
             100                 105                 110

Leu Ser Ala Ile Ser Thr Glu Arg Cys Leu Ser Val Leu Trp Pro Ile
         115                 120                 125

Trp Tyr Arg Cys Arg Arg Pro Thr His Leu Ser Ala Val Val Cys Val
     130                 135                 140

Leu Leu Trp Gly Leu Ser Leu Leu Phe Ser Met Leu Glu Trp Arg Phe
145                 150                 155                 160

Cys Asp Phe Leu Phe Ser Gly Ala Asp Ser Ser Trp Cys Glu Thr Ser
                 165                 170                 175

Asp Phe Ile Pro Val Val Trp Leu Ile Phe Leu Cys Val Val Leu Cys
             180                 185                 190

Val Ser Ser Leu Val Leu Leu Val Arg Ile Leu Cys Gly Ser Arg Lys
         195                 200                 205

Met Pro Leu Thr Arg Leu Tyr Val Thr Ile Leu Leu Thr Val Leu Val
     210                 215                 220

Phe Leu Leu Cys Gly Leu Pro Phe Gly Ile Leu Gly Ala Leu Ile Tyr
225                 230                 235                 240

Arg Met His Leu Asn Leu Glu Val Leu Tyr Cys His Val Tyr Leu Val
                 245                 250                 255

Cys Met Ser Leu Ser Ser Leu Asn Ser Ser Ala Asn Pro Ile Ile Tyr
             260                 265                 270

Phe Phe Val Gly Ser Phe Arg Gln Arg Gln Asn Arg Gln Asn Leu Lys
         275                 280                 285

Leu Val Leu Gln Arg Ala Leu Gln Asp Lys Pro Glu Val Asp Lys Gly
     290                 295                 300

Glu Gly Gln Leu Pro Glu Glu Ser Leu Glu Leu Ser Gly Ser Lys Leu
305                 310                 315                 320

Gly Pro

<210> SEQ ID NO 14
<211> LENGTH: 969
<212> TYPE: DNA
<213> ORGANISM: Homo sapiens

<400> SEQUENCE: 14
atggatccaa ccgtcccagt cttcggtaca aaactgacac caatcaacgg acgtgaggag      60
actccttgct acaatcagac cctgagcttc acggtgctga cgtgcatcat ttcccttgtc     120
ggactgacag gaaacgcggt tgtgctctgg ctcctgggct accgcatgcg caggaacgct     180
gtctccatct acatcctcaa cctggccgca gcagacttcc tcttcctcag cttccaaatt     240
atacgttcgc cattacgcct catcaatatc agccatctca tccgcaaaat cctcgtttct     300
gtgatgacct ttccctactt tacaggcctg agtatgctga gcgccatcag caccgagcgc     360
tgcctgtctg ttctgtggcc catctggtac cgctgccgcc gccccacaca cctgtcagcg     420
```

```
gtcgtgtgtg tcctgctctg gggcctgtcc ctgctgttta gtatgctgga gtggaggttc      480
tgtgacttcc tgtttagtgg tgctgattct agttggtgtg aaacgtcaga tttcatccca      540
gtcgtgtggc tgattttttt atgtgtggtt ctctgtgttt ccagcctggt cctgctggtc      600
aggatcctct gtggatcccg gaagatgccg ctgaccaggc tgtacgtgac catcctgctc      660
acagtgctgg tcttcctcct ctgcggcctg cccttcggca ttctggggc cctaatttac       720 aggatgcacc tgaatttgga agtcttatat tgtcatgttt atctggtttg catgtccctg      780
tcctctctaa acagtagtgc aaccccatc atttacttct tcgtgggctc ctttaggcag       840
cgtcaaaata ggcagaacct gaagctggtt ctccaaaggg ctctgcagga caagcctgag      900
gtggataaag gtgaagggca gcttcctgag gaaagcctgg agctgtcggg aagcaaattg      960
gggccatga                                                              969
```

<210> SEQ ID NO 15
<211> LENGTH: 35
<212> TYPE: DNA
<213> ORGANISM: synthetic PCR primer
<220> FEATURE:
<221> NAME/KEY: modified_base
<222> LOCATION: (1)..(35)
<223> OTHER INFORMATION: "n" is inosine

<400> SEQUENCE: 15

```
ggccgtcgac ttcatcgtcw myctnkcnyt ngcng                                 35
```

<210> SEQ ID NO 16
<211> LENGTH: 15
<212> TYPE: DNA
<213> ORGANISM: synthetic PCR primer
<220> FEATURE:
<221> NAME/KEY: modified_base
<222> LOCATION: (1)..(15)
<223> OTHER INFORMATION: "n" is inosine

<400> SEQUENCE: 16

```
rhwrcartan atnat                                                       15
```

<210> SEQ ID NO 17
<211> LENGTH: 25
<212> TYPE: DNA
<213> ORGANISM: synthetic PCR primer

<400> SEQUENCE: 17

```
cgcagatgag gtagtacagc atcac                                            25
```

<210> SEQ ID NO 18
<211> LENGTH: 25
<212> TYPE: DNA
<213> ORGANISM: synthetic PCR primer

<400> SEQUENCE: 18

```
ctgtgagaga gatggtaaca tacag                                            25
```

<210> SEQ ID NO 19
<211> LENGTH: 24
<212> TYPE: DNA
<213> ORGANISM: synthetic PCR primer

<400> SEQUENCE: 19

```
gcatccttga ctggttcttc tcag                                             24
```

-continued

```
<210> SEQ ID NO 20
<211> LENGTH: 25
<212> TYPE: DNA
<213> ORGANISM: synthetic PCR primer

<400> SEQUENCE: 20
gggtgagact catcatcatt tgtgg                                    25

<210> SEQ ID NO 21
<211> LENGTH: 30
<212> TYPE: DNA
<213> ORGANISM: synthetic PCR primer

<400> SEQUENCE: 21
gcaagctttc tgagcatgga tccaaccgtc                               30

<210> SEQ ID NO 22
<211> LENGTH: 30
<212> TYPE: DNA
<213> ORGANISM: synthetic PCR primer

<400> SEQUENCE: 22
ccctcagatc tccaatttgc ttcccgacag                               30
```

HUMAN G PROTEIN-COUPLED RECEPTOR EXPRESSED IN THE DORSAL ROOT GANGLIA

CROSS REFERENCE TO RELATED APPLICATIONS

The present application is a continuation of U.S. application Ser. No. 09/254,227, filed on Mar. 3, 1999 now U.S. Pat. No. 6,696,257. The '227 application represents U.S. national stage of international application PCT/SE98/02348, which had an international filing date of Dec. 16, 1998, and which was published in English under PCT Article 21(2) on Jul. 1, 1999. The international application claims priority to Swedish application no. 9704836-7, filed on Dec. 22, 1997.

FIELD OF THE INVENTION

The present invention is in the general field of biological receptors and the various uses that can be made of such receptors. More specifically, the invention relates to nucleic acids encoding novel G protein-coupled receptors and to the receptors per se.

BACKGROUND AND PRIOR ART

G protein-coupled receptors (GPCRs) constitute a family of proteins sharing a common structural organization characterized by an extracellular N-terminal end, seven hydrophobic alpha helices putatively constituting transmembrane domains and an intracellular C-terminal domain. GPCRs bind a wide variety of ligands that trigger intracellular signals through the activation of transducing G proteins (Caron, et al., Rec. Prog. Horm. Res. 48:277–290 (1993); Freedman et al., Rec. Prog. Horm. Res. 51:319–353 (1996)).

More than 300 GPCRs have been cloned thus far and it is generally assumed that there exist well over 1000 such receptors. Mechanistically, approximately 50–60% of all clinically relevant drugs act by modulating the functions of various GPCRs (Cudermann, et al., J. Mol. Med. 73:51–63 (1995)). Of particular interest are receptors located in dorsal root ganglia. This region of the central nervous system is densely innervated with primary or afferent sensory neurons involved in the transmission, modulation and sensation of pain. Thus, receptors from this region may be used in assays for the identification of new agents for anesthesia and analgesia

SUMMARY OF THE INVENTION

The present invention is based upon the discovery of a novel G protein-coupled receptor which is distinct from previously reported receptors in terms of structure and in being expressed preferentially in dorsal root ganglia. One dorsal root receptor (DRR) has been isolated and sequenced from the rat and six from the human. The rat receptor was given the designation rDRR-1 and its amino acid sequence is shown as SEQ ID NO:1. The human receptors were designated as
hDRR-1 (SEQ ID NO:3);
hDRR-2 (SEQ ID NO:5);
hDRR-3 (SEQ ID NO:7):
hDRR-4 (SEQ ID NO:9);
hDRR-5 (SEQ ID NO:11); and
hDRR-6 (SEQ ID NO:13).
Unless otherwise specified, the term "DRR" as used herein refers to all of the receptors from both human and rat.

In its first aspect, the invention is directed to proteins, except as existing in nature, comprising the amino acid sequence consisting functionally of a rat or human DRR as shown in SEQ ID NO:1, 3, 5, 7, 9, 11, or 13. The term "consisting functionally of" is intended to include any receptor protein whose sequence has undergone additions, deletions or substitutions which do not substantially alter the functional characteristics of the receptor. Thus, the invention encompasses proteins having exactly the same amino acid sequence as shown in the sequence listing, as well as proteins with differences that are not substantial as evidenced by their retaining the basic, qualitative binding properties of the DRR receptor. The invention further encompasses substantially pure proteins consisting essentially of a DRR amino acid sequence, antibodies that bind specifically to a DRR (i.e. that have at least a 100 fold greater affinity for the DRR than any other naturally occurring non-DRR protein), and antibodies made by a process involving the injection of pharmaceutically acceptable preparations of such proteins into an animal capable of antibody production. In a preferred embodiment, monoclonal antibody to human or rat DRR is produced by injecting a pharmaceutically acceptable preparation of the receptor into a mouse and then fusing mouse spleen cells with myeloma cells.

The invention is also directed to a substantially pure polynucleotide encoding a protein comprising the amino acid sequence consisting functionally of the sequence of rat DRR (as shown in SEQ ID NO:1) or a human DRR (as shown in SEQ ID NOs 3, 5, 7, 9, 11 or 13). This aspect of the invention encompasses polynucleotides encoding proteins consisting essentially of the amino acid sequences shown in the sequence listing, expression vectors comprising such polynucleotides, and host cells transformed with such vectors. Also included are the recombinant rat and human DRR proteins produced by host cells made in this manner.

Preferably, the polynucleotide encoding rat DRR has the nucleotide sequence shown in SEQ ID NO:2 and the polynucleotide encoding a human DRR has the nucleotide sequence shown in SEQ ID NO:3, 5, 7, 9, 11 or 13. It is also preferred that the vectors and host cells used for the expression of DRR contain these particular polynucleotides.

In another aspect, the present invention is directed to a method for assaying a test compound for its ability to bind to a rat or human DRR. The method is performed by incubating a source of DRR with a ligand known to bind to the receptor and with the test compound. The source of the DRR should be substantially free of other types of G protein-coupled receptors, i.e. greater than 85% of such receptors present should correspond to the DRR. Upon completion of incubation, the ability of the test compound to bind to the DRR is determined by the extent to which ligand binding has been displaced. The rat DRR should, preferably correspond to rDRR-1 as shown in SEQ ID NO:1. The human receptor should preferably be hDRR-1 (SEQ ID NO:3); hDRR-2 (SEQ ID NO:5); hDRR-3 (SEQ ID NO:7); hDRR-4 (SEQ ID NO:9); hDRR-5 (SEQ ID NO:11); or hDRR-6 (SEQ ID NO:13). Either transformed cells expressing recombinant DRR may be used in the assays or membranes can be prepared from the cells and used. Although not essential, the assay can be accompanied by the determination of the activation of a second messenger pathway such as the adenyl cyclase pathway. This should help to determine whether a compound that binds to DRR is acting as an agonist or antagonist.

An alternative method for determining if a test compound is an agonist of any of the DRRs disclosed herein is to use a cell signaling assay, e.g., an assay measuring either intracellular adenyl cyclase activity or intracellular calcium concentration. The test compound is incubated with cells expressing the DRR but substantially free of other G protein-coupled receptors, typically a cell transfected with an expression vector encoding the DRR. Test compounds that are agonists are identified by their causing a statistically significant change in the results obtained from the cell signaling assay when compared to control transfectants not exposed to test compound. For example, the cells exposed to the test compound may show a significant increase in adenyl cyclase activity or in intracellular calcium concentration.

The invention also encompasses a method for determining if a test compound is an antagonist of a DRR which relies upon the known activation of G protein-coupled receptors that occurs when such receptors are expressed in large amounts. This method requires that DNA encoding the receptor be incorporated into an expression vector so that it is operably linked to a promoter and that the vector then be used to transfect an appropriate host. In order to produce sufficient receptor to result in constitutive receptor activation (i.e., activation in the absence of natural ligand), expression systems capable of copious protein production are preferred, e.g., the DRR DNA may be operably linked to a CMV promoter and expressed in COS or HEK293 cells. After transfection, cells with activated receptors are selected based upon their showing increased activity in a cell signaling assay relative to comparable cells that have either not been transfected or that have been transfected with a vector that is incapable of expressing functional DRR. Typically, cells will be selected either because they show a statistically significant increase in intracellular adenyl cyclase activity or a statistically significant increase in intracellular calcium concentration. The selected cells are contacted with the test compound and the cell signaling assay is repeated to determine if this results in a decrease in activity relative to control cells not contacted with the test compound. For example, a statistically significant decrease in either adenyl cyclase activity or calcium concentration relative to control cells would indicate that the test compound is an antagonist of the DRR. Any of the DRRs disclosed herein may be used in these assays.

Assays for compounds interacting with a DRR may be performed by incubating a source containing the DRR but substantially free of other G protein-coupled receptors (e.g. a stably transformed cell) with angiotensin II or III in both the presence and absence of test compound and measuring the modulation of intracellular calcium concentration. A significant increase or decrease in angiotensin-stimulated calcium displacement in response to test compound is indicative of an interaction occurring at the DRR. The receptors that may be used in these assays include rat DRR-1 and human DRR-1, DRR-2, DRR-3, DRR-4, DRR-5 and DRR-6.

In another aspect, the present invention is directed to a method for assaying a test compound for its ability to alter the expression of a rat or human DRR. This method is performed by growing cells expressing the DRR, but substantially free of other G protein-coupled receptors, in the presence of the test compound. Cells are then collected and the expression of the DRR is compared with expression in control cells grown under essentially identical conditions but in the absence of the test compound. The rat receptor is preferably rDRR-1 and the human receptor may be DRR-1; DRR-2; DRR-3; DRR-4; DRR-5; or DRR-6.

A preferred test compound is an oligonucleotide at least 15 nucleotides in length comprising a sequence complimentary to the sequence of the DRR used in the assay.

BRIEF DESCRIPTION OF THE DRAWINGS

FIG. 1. Nucleotide sequence of rDRR-1: Clone 3B-32, encoding rDRR-1 was isolated from a rat genomic library using the Promoter Finder Walking Kit (see Methods, Clontech).

The cloned gene was deposited with the international depositary authority Deutsche Sammlung Von Mikroorganismen Und Zellkulturen GmbH at the address Mascheroder Weg 1 B, D-3300 Braunschweig, Germany. The deposit was made on Nov. 27, 1997 and was given the accession number DSM 11877.

FIG. 2. Deduced amino acid sequence of DRR-1: Clone 3B-32 codes for a 337 amino acid protein. The amino acid sequence begins; with the first ATG in the nucleotide sequence.

Figure 3A:
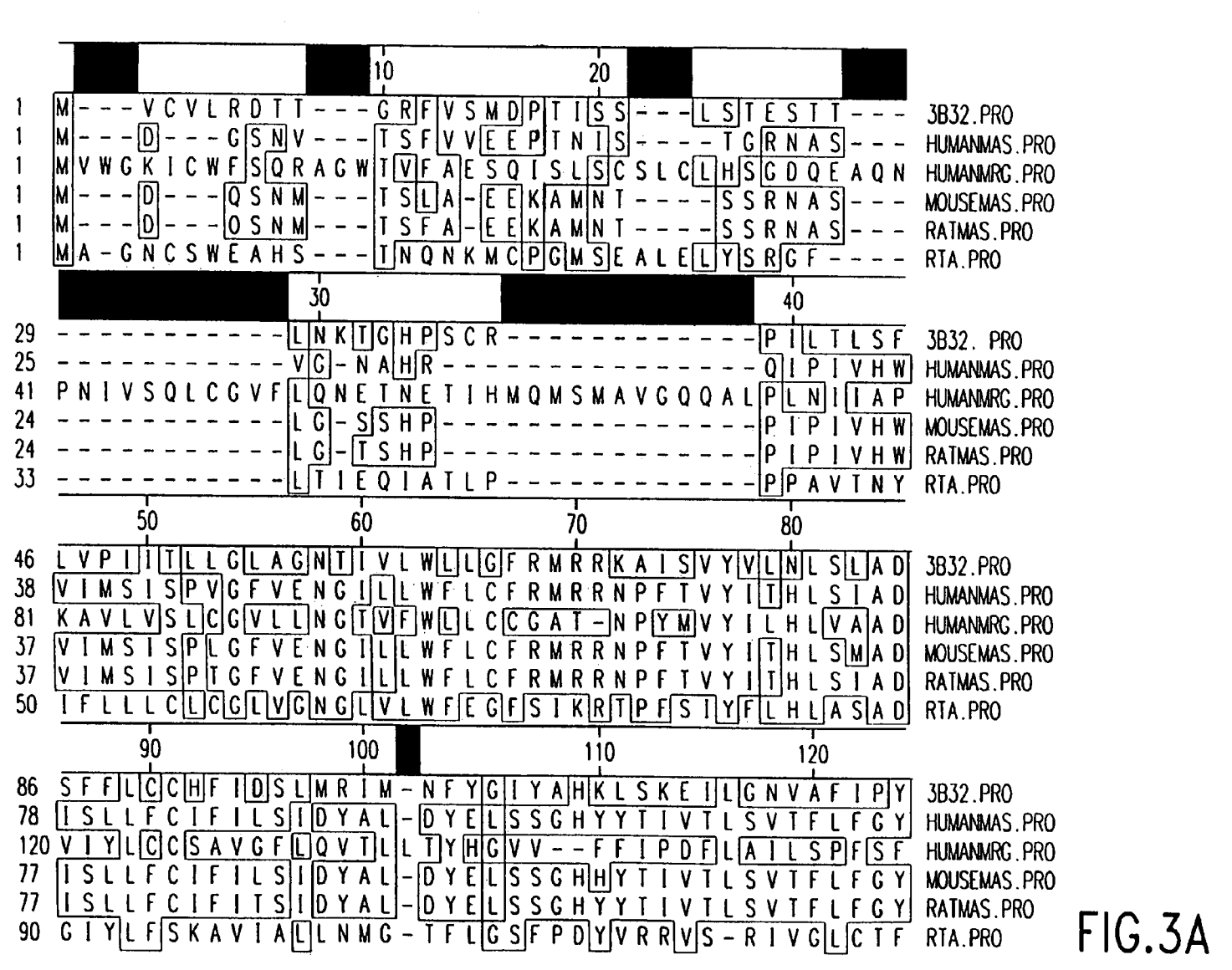
Figure 3B:
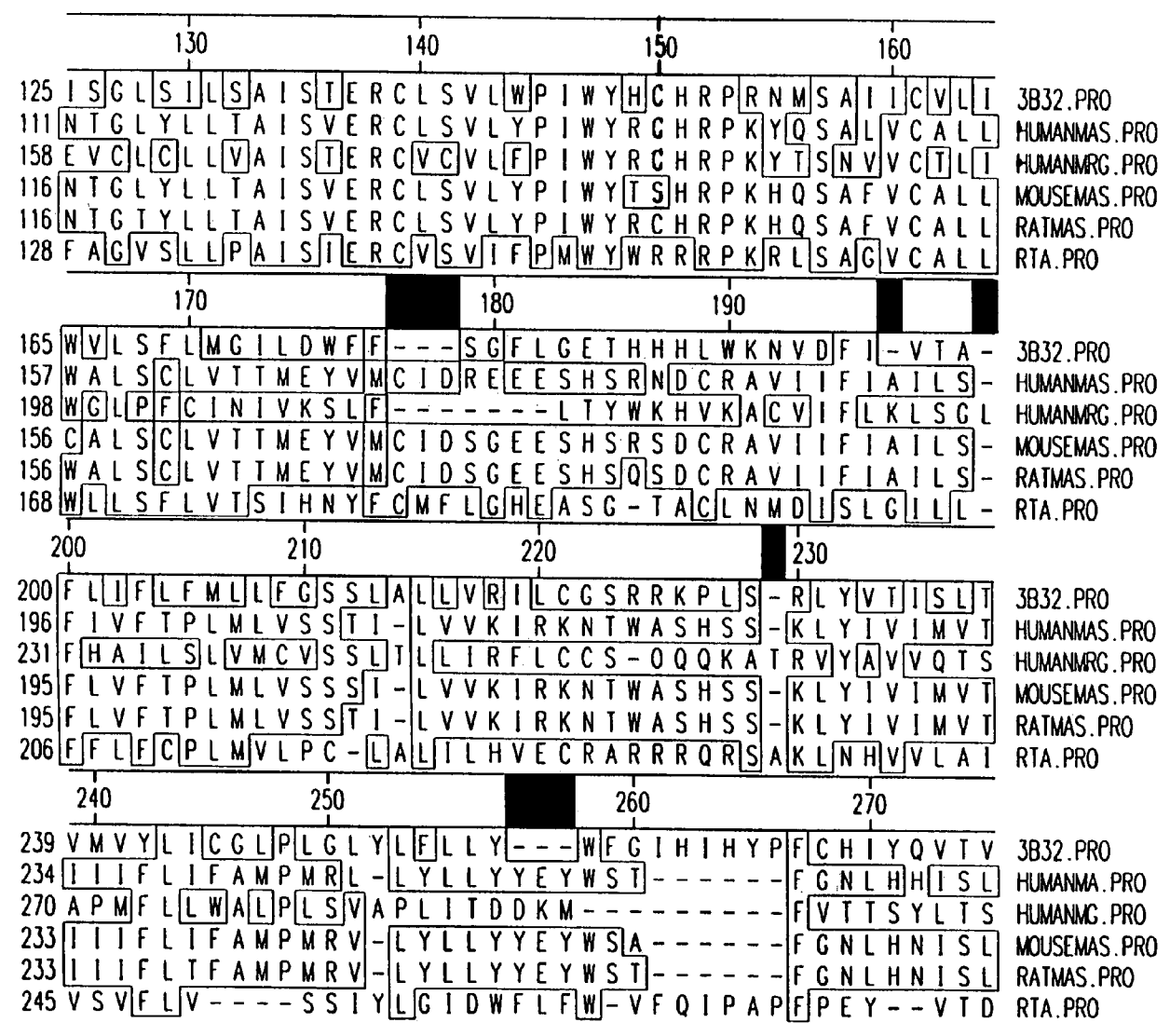

FIG. 3A–3C. Alignment of the deduced amino acid sequences of clone 3B-32 (rDRR-1) with its five most homologous sequences. The boxed and shaded residues are the ones that are identical to the rDRR-1 sequence.

Figure 4A:
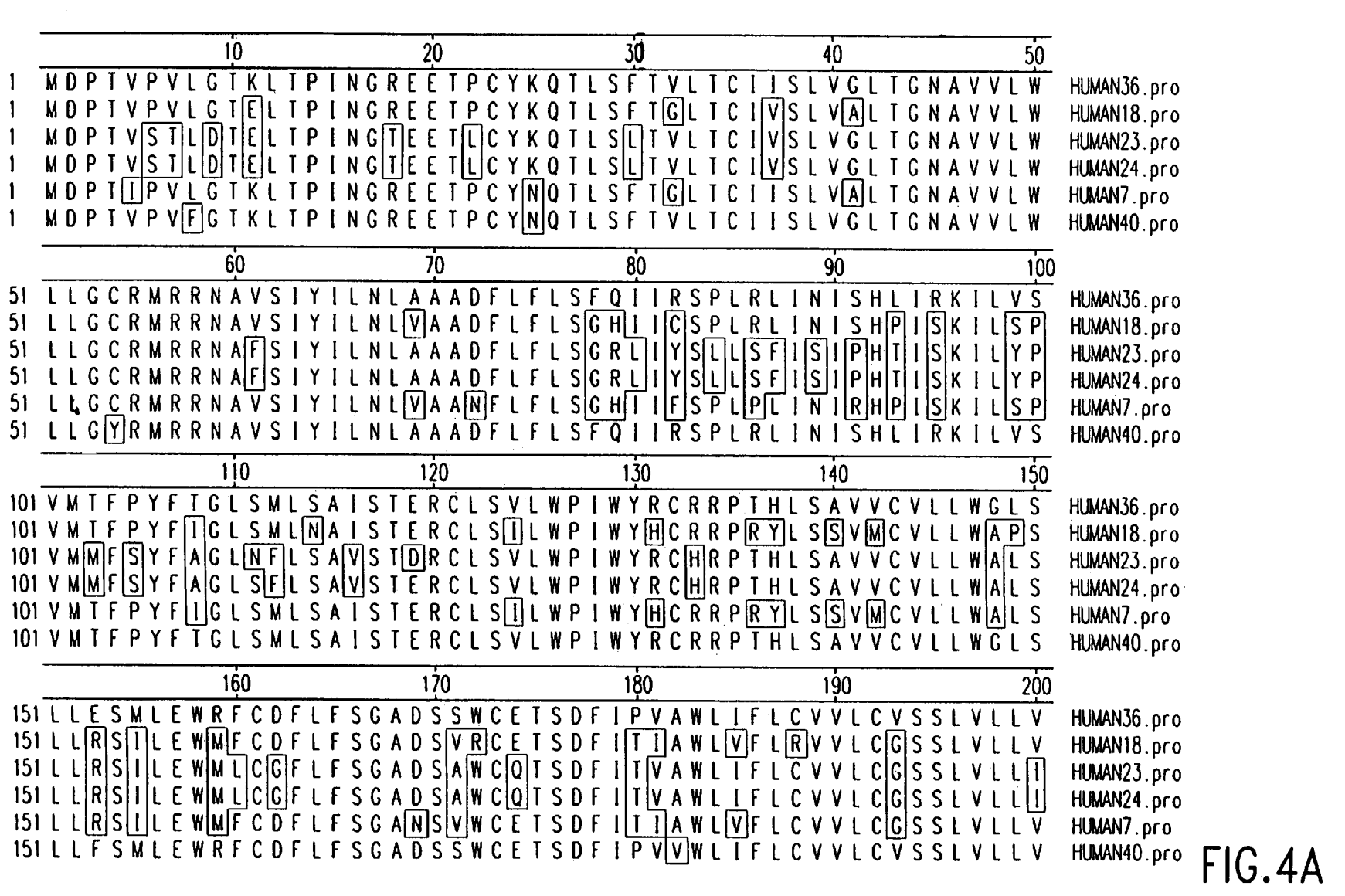

FIG. 4A–4B. Amino acid alignment of the human DRR homologs: The amino acid sequence of all 6 human homologs of rDRR-1 (hDRR-1; hDRR-2; hDRR-3; hDRR-4; hDRR-5; and hDRR-6 ) are aligned. The amino acid residues differing from the clone 36 (HUMAN36.PR) are boxed. The degree of identity among these sequences ranges from 77% to almost 100%.

DEFINITIONS

The description that follows uses a number of terms that refer to recombinant DNA technology. In order to provide a clear and consistent understanding of the specification and claims, including the scope to be given such terms, the following definitions are provided.

Cloning vector: A plasmid or phage DNA or other DNA sequence which is able to replicate autonomously in a host cell, and which is characterized by one or a small number of restriction endonuclease recognition sites. A foreign DNA fragment may be spliced into the vector at these sites in order to bring about the replication and cloning of the fragment. The vector may contain a marker suitable for use in the identification of transformed cells. For example, markers may provide tetracycline resistance or ampicillin resistance.

Expression vector: A vector similar to a cloning vector but which is capable of inducing the expression of the DNA that has been cloned into it, after transformation into a host. The cloned DNA is usually placed under the control of (i.e., operably linked to) certain regulatory sequences such as promoters or enhancers. Promoter sequences may be constitutive, inducible or repressible.

Substantially pure: As used herein, "substantially pure" means that the desired product is essentially free from contaminating cellular components. A "substantially pure" protein or nucleic acid will typically comprise at least 85% of a sample, with greater percentages being preferred. Contaminants may include proteins, carbohydrates or lipids. One method for determining the purity of a protein or nucleic acid is by electrophoresing a preparation in a matrix such as polyacrylamide or agarose. Purity is evidenced by the appearance of a single band after staining. Other methods for assessing purity include chromatography and analytical centrifugation.

Host: Any prokaryotic or eukaryotic cell that is the recipient of a replicable expression vector or cloning vector is the "host" for that vector. The term encompasses prokaryotic or eukaryotic cells that have been engineered to incorporate a desired gene on its chromosome or in its genome. Examples of cells that can serve as hosts are well known in the art, as are techniques for cellular transformation (see e.g. Sambrook et al., Molecular Cloning: A Laboratory Manual, 2nd ed. Cold Spring Harbor (1989)).

Promoter: A DNA sequence typically found in the 5 region of a gene, located proximal to the start codon. Transcription is initiated at the promoter. If the promoter is of the inducible type, then the rate of transcription increases in response to an inducing agent.

Complementary Nucleotide Sequence: A complementary nucleotide sequence, as used herein, refers to the sequence that would arise by normal base pairing. For example, the nucleotide sequence 5-AGAC-3 would have the complementary sequence 5-GTCT-3.

Expression: Expression is the process by which a polypeptide is produced from DNA. The process involves the transcription of the gene into mRNA and the translation of this mRNA into a polypeptide.

DETAILED DESCRIPTION OF THE INVENTION

The present invention is directed to DRR receptor proteins, genetic sequences coding for the receptors, a method for assaying compounds for binding to DRR receptors and a method for assaying compounds for their ability to alter DRR expression. The receptors and their nucleic acids are defined by their structures (as shown in FIGS. 1, 2 and 4; and SEQ ID numbers 1–14).

It will be understood that the present invention encompasses not only sequences identical to those shown in the figures and sequence listing, but also sequences that are essentially the same and sequences that are otherwise substantially the same and which result in a receptor retaining the basic binding characteristics of the DRR. For example, it is well known that techniques such as site-directed mutagenesis may be used to introduce variations in a protein's structure. Variations in a DRR protein introduced by this or some similar method are encompassed by the invention provided that the resulting receptor retains the basic qualitative binding characteristics of the unaltered DRR. Thus, the invention relates to proteins comprising amino acid sequences consisting functionally of the sequence of SEQ ID NO:1 (rat) and SEQ ID numbers 3, 5, 7, 9, 11 and 14 (human).

I. Nucleic Acid Sequences Coding for DRR

DNA sequences coding for DRRs are expressed exclusively, or at least highly preferentially, in dorsal root ganglia and these ganglia may serve as a source for the isolation of nucleic acids coding for the receptors. In addition, cells and cell lines that express a rat or human DRR may serve as a source for nucleic acid. These may either be cultured cells that have not undergone transformation or cell lines specifically engineered to express recombinant DRR.

In all cases, poly A+ mRNA is isolated from the dorsal root ganglia, reverse transcribed and cloned. The cDNA library thus formed may then be screened using probes derived from the sequences shown in the accompanying sequence listing as SEQ ID number 2, 4, 6, 8, 10 12 or 14, depending upon the particular DRR being isolated. Probes should typically be at least 14 bases in length and should be derived from a portion of the DRR sequence that is poorly conserved (see FIGS. 3 and 4). Screening can also be performed using genomic libraries with one DRR gene, or a portion of the gene, serving as a probe in the isolation of other DRR genes. For example, full length rDRR-1 may be labeled and used to screen a human genomic library for the isolation of hDRR-1, hDRR-2 etc. (see Examples section).

Alternatively genomic DNA libraries can be used to isolate DRR genes by performing PCR amplifications with primers located at either end of genes (see Examples section for a description of procedures). For example, human genomic DNA may be amplified using the primers:

5'-GCAAGCTTTCTGAGCATGGATCCAACCGTC, and

5'-CCCTCAGATCTCCAATTTGCTTCCCGACAG.

This will serve to amplify all six of the human DRR genes identified herein as hDRR-1; hDRR-2; hDRR-3; hDRR-4; hDRR-5; and hDRR-6. These may then be cloned into an appropriate vector, e.g. pGEM-T (Promega), for DNA sequence analysis.

II. Antibodies to Rat and Human DRRs

The present invention is also directed to antibodies that bind specifically to a rat or human DRR and to a process for producing such antibodies. Antibodies that "bind specifically to a DRR" are defined as those that have at least a one hundred fold greater affinity for the DRR than for any other protein. The process for producing such antibodies may involve either injecting the DRR protein itself into an appropriate animal or, preferably, injecting short peptides made to correspond to different regions of the DRR. The peptides should be at least five amino acids in length and should be selected from regions believed to be unique to the particular DRR protein being targeted. Thus, highly conserved transmembrane regions should generally be avoided in selecting peptides for the generation of antibodies. Methods for making and detecting antibodies are well known to those of skill in the art as evidenced by standard reference works such as: (Harlow et al., *Antibodies, A Laboratory Manual*, Cold Spring Harbor Laboratory, N.Y. (1988)); Klein, *Immunology: The Science of Self-Nonself Discrimination* (1982); Kennett, et al., *Monoclonal Antibodies and Hybridomas: A New Dimension in Biological Analyses* (1980); and Campbell, "*Monoclonal Antibody Technology*," *in Laboratory Techniques in Biochemistry and Molecular Biology*, (1984)).

"Antibody," as used herein, is meant to include intact molecules as well as fragments which retain their ability to bind to antigen (e.g., Fab and F(ab)2 fragments). These fragments are typically produced by proteolytically cleaving intact antibodies using enzymes such as papain (to produce Fab fragments) or pepsin (to produce F(ab)2 fragments). The term "antibody" also refers to both monoclonal antibodies and polyclonal antibodies. Polyclonal antibodies are derived from the sera of animals immunized with the antigen. Monoclonal antibodies can be prepared using hybridoma technology (Kohler, et al., *Nature* 256:495 (1975); Hammerling, et al., in: *Monoclonal Antibodies and T-Cell Hybridomas*, Elsevier, M. Y., pp. 563–681 (1981)). In general, this technology involves immunizing an animal, usually a mouse, with either intact DRR or a fragment derived from the DRR. The splenocytes of the immunized animals are extracted and fused with suitable myeloma cells, e.g., SP2O cells. After fusion, the resulting hybridoma cells are selectively maintained in HAT medium and then cloned by limiting dilution (Wands; et al., Gastroenterology 80:225–232 (1981)). The cells obtained through such selection are then assayed to identify clones which secrete antibodies capable of binding to the DRR.

The antibodies, or fragments of antibodies, of the present invention may be used to detect the presence of DRR protein using any of a variety of immunoassays. For example, the antibodies may be used in radioimmunoassays or in immunometric assays, also known as "two-site" or "sandwich" assays (see Chard, T., "*An Introduction to Radioimmune Assay and Related Techniques,*"*in Laboratory Techniques in Biochemistry and Molecular Biology*, North Holland Publishing Co., N.Y. (1978)). In a typical immunometric assay, a quantity of unlabeled antibody is bound to a solid support that is insoluble in the fluid being tested, e.g., blood, lymph, cellular extracts, etc. After the initial binding of antigen to immobilized antibody, a quantity of detectably labeled second antibody (which may or may not be the same as the first) is added to permit detection and/or quantitation of bound antigen (see e.g. Radioimmune Assay Method, Kirkham et al., ed., pp. 199–206, E & S. Livingstone, Edinburgh (1970)). Many variations of these types of assays are known in the art and may be employed for the detection of the DRR.

Antibodies to a rat or human DRR may also be used in the purification of either the intact receptor or fragments of the receptor (see generally, Dean et al., *Affinity Chromatography, A Practical Approach*, IRL Press (1986)). Typically, antibody is immobilized on a chromatographic matrix such as Sepharose 4B. The matrix is then packed into a column and the preparation containing the DRR desired is passed through under conditions that promote binding, e.g., under conditions of low salt. The column is then washed and bound DRR is eluted using a buffer that promotes dissociation from antibody, e.g., buffer having an altered pH or salt concentration. The eluted DRR may be transferred into a buffer of choice, e.g., by dialysis, and either stored or used directly.

III. Radioligand Assay for Receptor Binding

One of the main uses for DRR nucleic acids and recombinant proteins is in assays designed to identify agents capable of binding to DRR receptors. Such agents may either be agonists, mimicking the normal effects of receptor binding, or antagonists, inhibiting the normal effects of receptor binding. Of particular interest is the identification of agents which bind to the DRR and modulate adenyl cyclase activity in the cells. These agents have potential therapeutic application as either analgesics or anesthetics. In radioligand binding assays, a source of DRR is incubated together with a ligand known to bind to the receptor and with the compound being tested for binding activity. The preferred source for DRR is cells, preferably mammalian cells, transformed to recombinantly express the receptor. The cells selected should not express a substantial amount of any other G protein-coupled receptors that might bind to ligand and distort results. This can easily be determined by performing binding assays on cells derived from the same tissue or cell line as those recombinantly expressing DRR but which have not undergone transformation.

The assay may be performed either with intact cells or with membranes prepared from the cells (see e.g. Wang, et al., *Proc. Natl. Acad. Sci. U.S.A.* 90:10230–10234 (1993)). The membranes are incubated with a ligand specific for the DRR receptor and with a preparation of the compound being tested. After binding is complete, receptor is separated from the solution containing ligand and test compound, e.g. by filtration, and the amount of binding that has occurred is determined. Preferably, the ligand used is detectably labeled with a radioisotope such as 125I. However, if desired, fluorescent or chemiluminescent labels can be used instead. Among the most commonly used fluorescent labeling compounds are fluorescein isothiocynate, rhodamine, phycoerythrin, phycocyanin, allophycocyanin, o-phthaldehyde and fluorescamine. Useful chemiluminescent compounds include luminol, isoluminol, theromatic acridinium ester, imidazole, acridinium salt, and oxalate ester. Any of these agents which can be used to produce a ligand suitable for use in the assay.

Nonspecific binding may be determined by carrying out the binding reaction in the presence of a large excess of unlabeled ligand. For examples labeled ligand may be incubated with receptor and test compound in the presence of a thousandfold excess of unlabeled ligand. Nonspecific binding should be subtracted from total binding, i.e. binding in the absence of unlabeled ligand, to arrive at the specific binding for each sample tested. Other steps such as washing, stirring, shaking, filtering and the like may be included in the assays as necessary. Typically, wash steps are included after the separation of membrane-bound ligand from ligand remaining in solution and prior to quantitation of the amount of ligand bound, e.g., by counting radioactive isotope. The specific binding obtained in the presence of test compound is compared with that obtained in the presence of labeled ligand alone to determine the extent to which the test compound has displaced receptor binding.

In performing binding assays, care must be taken to avoid artifacts which may make it appear that a test compound is interacting with the. DRR receptor when, in fact, binding is being inhibited by some other mechanism. For example, the compound being tested should be in a buffer which does not itself substantially inhibit the binding of ligand to DRR and should, preferably, be tested at several different concentrations. Preparations of test compound should also be examined for proteolytic activity and it is desirable that antiproteases be included in assays. Finally, it is highly desirable that compounds identified as displacing the binding of ligand to DRR receptor be reexamined in a concentration range sufficient to perform a Scatchard analysis on the results. This type of analysis is well known in the art and can be used for determining the affinity of a test compounds for receptor (see e.g., Ausubel, et al., *Current Protocols in Molecular Biology*, 11.2.1–11.2.19 (1993); *Laboratory Techniques and Biochemistry and Molecular Biology, Work*, et al., ed., N.Y. (1978) etc.). Computer programs may be used to help in the analysis of results (see e.g., Munson, P., *Methods Enzymol.* 92:543–577 (1983); McPherson, G. A., *Kinetic, EBDA Ligand, Lowry—A Collection of Radioligand Binding Analysis Programs*, Elsevier-Biosoft, U.K. (1985)).

The activation of receptor by the binding of ligand may be monitored using a number of different assays. For example, adenyl cyclase assays may be performed by growing cells in wells of a microtiter plate and then incubating the various wells in the presence or absence of test compound. cAMP may then be extracted in ethanol, lyophilized and resuspended in assay buffer. Assay of cAMP thus recovered may be carried out using any method for determining cAMP concentration, e.g. the Biotrack cAMP Enzyme-immunoassay System (Amersham) or the Cyclic AMP [3H] Assay System (Amersham). Typically, adenyl cyclase assays will be performed separately from binding assays, but it may also be possible to perform binding and adenyl cyclase assays on a single preparation of cells. Other "cell signaling assays" that can be used to monitor receptor activity are described below.

IV. Identification of DRR Agonists and Antagonists Using Cell Signaling Assays

DRRs may also be used to screen for drug candidates using cell signaling assays. To identify DRR agonists, the DNA encoding a receptor is incorporated into an expression vector and then transfected into an appropriate host. The transformed cells are then contacted with a series of test compounds and the effect of each is monitored. Among the assays that can be used are assays measuring cAMP production (see discussion above), assays measuring the activation of reporter gene activity, or assays measuring the modulation of the binding of GTP-gamma-S.

Cell signaling assays may also be used to identify DRR antagonists. G protein-coupled receptors can be put in their active state even in the absence of their cognate ligand by expressing them at very high concentration in a heterologous system. For example, receptor may be overexpressed using the baculovirus infection of insect Sf9 cells or a DRR gene may be operably linked to a CMV promoter and expressed in COS or HEK293 cells. In this activated constitutive state, antagonists of the receptor can be identified in the absence of ligand by measuring the ability of a test compound to inhibit constitutive cell signaling activity. Appropriate assays for this are, again, cAMP assays, reporter gene activation assays or assays measuring the binding of GTP-gamma-S.

One preferred cell signaling assay is based upon the observation that cells stably transfected with DRRs show a change in intracellular calcium levels in response to incubation in the presence of angiotensin II or III (see Example 5). Thus, a procedure can be used to identify DRR agonists or antagonists that is similar to the radioreceptor assays discussed above except that angiotensin II or III is used instead of a labeled ligand and calcium concentration is measured instead of bound radioactivity. The concentration of calcium in the presence of test compound and angiotensin II or III is compared with that in the presence of angiotensin II or III alone to determine whether the test compound is interacting at the DRR receptor. A statistically significant increase in intracellular calcium in response to test compound indicates that the test compound is acting as an agonist whereas a statistically significant decrease in intracellular calcium indicates that it is acting as an antagonist.

V. Assay for Ability to Modulate DRR Expression

One way to either increase or decrease the biological effects of a DRR is to alter the extent to which the receptor is expressed in cells. Therefore, assays for the identification of compounds that either inhibit or enhance expression are of considerable interest. These assays are carried out by growing cells expressing a DRR in the presence of a test compound and then comparing receptor expression in these cells with expression in cells grown under essentially identical conditions but in the absence of the test compound. As in the binding assays discussed above, it is desirable that the cells used be substantially free of competing G protein-coupled receptors. One way to quantitate receptor expression is to fuse the DRR sequence to a sequence encoding a peptide or protein that can be readily quantitated. For example, the DRR sequence may be ligated to a sequence encoding haemaglutinin as described in Example 5 and used to stably transfect cells. After incubation with test compound the hemagglutininn/receptor complex can be immunoprecipitated and western blotted with anti-haemaglutinin antibody. Alternatively, Scatchard analysis of binding assays may be performed with labeled ligand to determine receptor number. The binding assays may be carried out as discussed above and will preferably utilize cells that have been engineered to recombinantly express DRR.

A preferred group of test compounds for inclusion in the DRR expression assay consists of oligonucleotides complementary to various segments of the DRR nucleic acid sequence. These oligonucleotides should be at least 15 bases in length and should be derived from non-conserved regions of the receptor nucleic acid sequence. Sequences may be based upon those shown as SEQ ID numbers 2, 4, 6, 8, 10, 12 or 14.

Oligonucleotides which are found to reduce receptor expression may be derivatized or conjugated in order to increase their effectiveness. For example, nucleoside phosphorothioates may be substituted for their natural counterparts (see Cohen, J., Oligodeoxynucleotides, Antisense Inhibitors of Gene Expression, CRC Press (1989)). The oligonucleotides may be delivered to a patient in vivo for the purpose of inhibiting DRR expression. When this is done, it is preferred that the oligonucleotide be administered in a form that enhances its uptake by cells. For example, the oligonucleotide may be delivered by means of a liposome or conjugated to a peptide that is ingested by cells (see e.g., U.S. Pat. Nos. 4,897,355 and 4,394,448; see also non-U.S. patent documents WO 8903849 and EP 0263740). Other methods for enhancing the efficiency of oligonucleotide delivery are well known in the art and are also compatible with the present invention.

Having now described the invention, the same will be more readily understood through reference to the following Examples which are provided by way of illustration and which are not intended to limit the scope of the invention.

EXAMPLES

Example 1

Cloning of Rat DRR-1

Isolation of cDNA Fragment.

Degenerate oligonucleotides were synthesized to highly conserved regions of G-protein coupled receptors (transmembrane spanning domains 2 and 7) with the following nucleotide sequences:

```
5' GG CCG TCG ACT TCA TCG TC(A/T)        SEQ ID NO:15
(A/C)(T/C)C TI(G/T) CI(T/C) TIG
C(A/C/G/T)G 3' (TM2:sense); and 5' (A/G)(C/A/T)(A/T) (A/G)CA (A/G)TA     SEQ ID NO:16
IAT IAT IGG (A/G)TT 3' (TM7:anti-
sense).
```

Poly A+ mRNA was isolated from cultured fetal rat dorsal root ganglia (Sprague-Dawley). The mRNA was reverse transcribed using the First Strand cDNA Synthesis kit (Pharmacia Biotech), subjected to an amplification reaction by polymerase chain reaction (PCR) using Ampli-Taq DNA (Perkin-Elmer Cetus) polymerase under the following conditions: 3 minutes at 94° C., 40 cycles of 1 minute at 94° C., 45° C. and 72° C. A cDNA PCR fragment corresponding to approximately 650 bps was isolated and subcloned in pGEM-T-vector (Promega Corporation). The nucleotide sequence of the recombinant clone was determined using the T7-dideoxy chain termination sequencing kit (Pharmacia Biotech) and was found to be unique based upon searches of Genbank/EMBL databases.

The full length rat DRR-1 sequence was obtained from rat genomic DNA using the 650 base pair fragment and the "Promoter Finder DNA Walking kit" (Clontech, cat # K1806-1). This kit contains five libraries of uncloned, adaptor-ligated genomic DNA fragments. The procedure involves two consecutive PCR reactions. Both reactions were done using the "Advantage Tth Polymerase Mix" also obtained from Clontech, following the conditions recommended by the vendor. The first PCR reaction was performed with the outer adaptor primer (AP1) provided in the kit and an outer, gene-specific primer (GSPI) derived from the sequence of the DRR-1 PCR fragment. The primary PCR mixtures were diluted and used as a template for the secondary (nested) PCR reaction with the nested adapter primer (AP2) and a nested gene specific primer (GSP2). To obtain the sequence of the rat DRR-1 gene upstream of the sequence of the original PCR fragment, the following oligonucleotides were used:

```
GSP1: oligo YF3B59-B,
5'-CGCAGATGAGGTAGTACAGCATCAC      SEQ ID NO:17

GSP2: oligo MML-R1,
5'-CTGTGAGAGAGATGGTAACATACAG      SEQ ID NO:18
```

From the first library, a fragment AP2-MMLR1 of 1.9 Kb was obtained and from the third library, a fragment of approximately 1.0 Kb was obtained. To identify the sequence downstream of the known sequence, the following primers were used:

```
GSP1: oligo YF3B59-F2,
5'-GCATCCTTGACTGGTTCTTCTCAG       SEQ ID NO:19

GSP2: oligo MML-F1,
5'-GGGTGAGACTCATCATCATTTGTGG.     SEQ ID NO:20
```

A fragment MMLF1-AP2 of approximately 1 Kb was obtained from the first library and a fragment of about 600 bp was obtained from the third library. The composite sequence of 1154 nucleotides containing the complete predicted open reading frame of DRR-1 is shown in FIG. 1. The open reading frame codes for a 337 amino acid protein (FIG. 2) with a predicted molecular mass of 38.7 kD. The protein sequence contains all the characteristic features of G protein-coupled receptors: seven hydrophobic helices likely to represent transmembrane domains, potential glycosylation site at the N-terminal extracellular domain (position 30) and a conserved NPXXY sequence at position 285–289.

Example 2

Cloning of Human DRR Receptor Genes

Two approaches were used to identify and clone novel human DNA sequences homologous and/or related to the rat DRR-1 gene. First, a human genomic library was screened in the lambda vector, Fix II, (Stratagene Cat.# 946203). Approximately 106 human genomic clones were plated and transferred onto nitrocellulose membranes for hybridization with the full length, 32P labeled, rat DRR-1 sequence as a probe. The hybridization was performed at 42° C., overnight. The filters were washed at room temperature at low stringency (1×SSC/0.1% SDS) to allow detection of related but not necessarily identical sequences.

The inserted human DNA present in positive phages was amplified by PCR using the "Expand PCR kit" from Boehringer-Mannheim under conditions allowing accurate amplification of very large fragments of DNA. These long fragments of DNA were digested with various restriction enzymes and subcloned into a plasmid vector. The portions of these clones which hybridized with the rat DRR-1 gene probe were sequenced using the ABI cycle sequencing kit.

A second approach to identifying novel human sequences related to DRR-1 involved the use of the polymerase chain reaction (PCR), performed on total human genomic DNA. Primers were synthesized based upon the human genomic clones described above and were as follows:

```
HML.H,
5'-GCAAGCTTTCTGAGCATGGATCCAACCGTC,     SEQ ID 21 and

HML.Bg,
5'-CCCTCAGATCTCCAATTTGCTTCCCGACAG,.    SEQ ID NO:22
```

Amplification resulted in a fragments of approximately 1 kilobase containing the entire coding sequence of the human genes. These fragments obtained were subcloned into the pGEM-T (Promega) vector for DNA sequencing analysis.

Using the above strategies, six human clones were isolated:

clone 7, SEQ ID numbers 3 and 4;
clone 18, SEQ ID numbers 5 and 6;
clone 23, SEQ ID numbers 7 and 8;
clone 24, SEQ ID numbers 9 and 10;
clone 36, SEQ ID numbers 11 and 12;and
clone 40, SEQ ID numbers 13 and 14.

None of these clones contain introns and their alignment may be seen in FIG. 3.

At the amino acid sequence level, the rat DRR-1 clone is 47% to 49% identical to the human clones.

At the nucleic acid level, the rat DRR-1 clone is 56% to 58% identical to the human clones. The level of sequence identity within the human clones (7, 18, 23, 24, 36, 40) is very high, between 77% and 98% at the amino acid sequence level. All the human sequences were used as queries to search for homologies in public databases (Genbank, Swissprot, EST). No identical sequences were detected. The closest matches were to members of the mas oncogene family of proteins. The overall amino acid sequence homology between rat DRR-1 and any of the isolated human genes varied from 47 to 50%. However some stretches display a much higher level of sequence homology, particularly the regions encoding the putative transmembrane domain III and VII (TM3 and TM7) and the intracellular loops 2 and 3 where the homology between the rat sequence and its human homologue is around 80%.

Example 3

In Situ Hybridization Experiments

Preparation of Tissue: Adult male Sprague-Dawley rats (~300 gm; Charles River, St-Constant, Quebec) were sacrificed by decapitation. Brain and spinal cord with dorsal root ganglia attached were removed, snap-frozen in isopentane at −40° C. for 20 s and stored at −80° C. Frozen human brain, spinal cord and dorsal root ganglia were obtained from the Brain and Tissue Bank for Developmental Disorders, University of Maryland at Baltimore, according to the strictest ethical guidelines. Frozen tissue was sectioned at 14 m in a Microm HM 500 M cryostat (Germany) and thaw-mounted onto ProbeOn Plus slides (Fisher Scientific, Montreal, Quebec). Sections were stored at −80° C. prior to in situ hybridization.

Synthesis of Riboprobes: The plasmid pGemT-3b32 GPCR was linearized using either SacII and Not 1 restriction enzymes. Sense and antisense DRR riboprobes were transcribed in vitro using either T7 or SP6 RNA polymerases (Pharmacia Biotech), respectively in the presence of [35S]UTP (~800 Ci/mmol; Amersham, Oakville, Ontario). The plasmid pGemT-Clone 36 GPCR was linearized using SacII and Pst 1 restriction enzymes. Sense and antisense Clon36 riboprobes were transcribed in vitro using either SP6 or T7 RNA polymerases (Pharmacia Biotech), respectively in the presence of [35S]UTP. Following transcription, the DNA template was digested with DNAse I (Pharmacia). Riboprobes were purified by phenol/chloroform/isoamyl alcohol extraction and precipitated in 70% ethanol containing ammonium acetate and tRNA. Quality of labeled riboprobes was verified by polyacrylamide-urea gel electrophoresis.

In situ Hybridization: Sections were postfixed in 4% paraformaldehyde (BDH, Poole, England) in 0.1 M phosphate buffer (pH 7.4) for 10 min at room temperature (RT) and rinsed in three changes of 2× standard sodium citrate buffer (SSC; 0.15 M NaCl. 0.015 M sodium citrate, pH 7.0). Sections were then equilibrated in 0.1 M triethanolamine, treated with 0.25% acetic anhydride in triethanolamine, rinsed in 2×SSC and dehydrated in an ethanol series (50–100%). Hybridization was performed in a buffer containing 75% formamide (Sigma, St-Louis, Mo.), 600 mM NaCl, 10 mM Tris (pH 7.5), 1 mM EDTA, 1× Denhardt's solution (Sigma), 50 (g/ml denatured salmon sperm DNA (Sigma), 50 (g/ml yeast tRNA (Sigma), 10% dextran sulfate (Sigma), 20 mM dithiothreitol and [35S]UTP-labeled cRNA probes (10×106 cpm/ml) at 55° C. for 18 h in humidified chambers. Following hybridization, slides were rinsed in 2×SSC at RT, treated with 20 (g/ml RNase IA (Pharmacia) in RNase buffer (10 mM Tris, 500 mM NaCl, 1 mM EDTA, pH 7.5) for 45 min at RT and washed to a final stringency of 0.1×SSC at 65° C. Sections were then dehydrated and exposed to Kodak Biomax MR film for 21 days and/or dipped in Kodak NTB2 emulsion diluted 1:1 with distilled water and exposed for 4–6 weeks at 4° C. prior to development and counterstaining with cresyl violet acetate (Sigma).

Results: Of all regions examined within the neuraxis of the rat, DRR-1 mRNA was exclusively expressed in dorsal root ganglia. High resolution emulsion autoradiography showed accumulations of silver grains exclusively over small and some medium size neurons. This unique and highly restricted distribution pattern for DRR-1 was confirmed in the rat embryo. Sagittal section of an E17 rat fetus showed that DRR-1 mRNA is confined to DRGs. All other structures of the rat embryo were devoid of any specific hybridization signal reinforcing the highly selective nature of DRR-1 expression The expression of human Clone 36 receptor was present in human fetal dorsal root ganglia but not in spinal cord. Specific hybridization signal for Clone 36 was not detected in any of the human adult CNS tissues examined thus far. These include spinal cord, cortex, hippocampus, thalamus, substantia-nigra and periaqueductal gray (data not shown). Presence of Clone 36 mRNA in adult DRGs remains to be examined. Standard controls in which additional spinal cord with DRG sections were hybridized with rat DRR-1 antisense or Clone 36 sense 35S-labeled probes displayed no specific hybridization signal.

Example 4

Northern Blots

Commercial rat and human multiple Northern blots containing 2 g of polyA RNA from various tissues (Clontech) were used to determine the expression and distribution of the rat DRR-1 message and its human homologues. Radioactively labeled probes were prepared as follows: twenty five ng of a 650 bp 3b-32 PCR fragment derived from rat DRR-1 (see Example 1) or human clone 36 were random-prime labeled using the Ready-to-Go DNA labeling kit (Pharmacia Biotech) and [32P]CTP (3000 Ci/mmol/Amersham). The blot was prehybridized for 1 hour at 68° C. using Expresshyb (Clontech) followed by hybridization (2×106 cpm/ml of probe) for one hour using the same conditions. Blots were washed at room temperature in 2×SSC, 0.05% SDS for 30 min. followed by 3× washes in 0.2×SSC, 1% SDS at 50° C. for 60 min. and exposed at −80° C. to Kodak Biomax film for 6 days.

Expression and Distribution of rat DRR-1: All the rat tissues studied (heart, brain, spleen, lung, skeletal muscle, kidney and testis) were negative for the expression of DRR-1 following 2 weeks exposure whereas rat genomic Southern analysis revealed a 1.1 kb band when probed with the same cDNA fragment.

Expression and Distribution of Human Clone 36: Northern blots containing RNA from various human tissues were probed with a radio-labeled DNA fragment from clone 36. All the human tissues studied (human fetal brain, lung, liver and kidney and adult human cerebellum, cerebral cortex, medulla, occipital pole, frontal lobe, temporal lobe, putamen, spinal cord, amygdala, caudate nucleus, corpus callosum, hippocampus, total brain, subthalamic nucleus and thalamus) were negative for the expression of this receptor following 2 weeks exposure.

Example 5

Calcium Signaling in Response to Angiotensin I–III

The coding sequence of human clone 24 was transferred into a pcDNA3 vector and modified to add a haemaglutinin tag at the C-terminus of the receptor sequence. This clone, designated as pcDNA3-HML-HA24 was transfected into HEK293 cells using a modified $CaCl_2$ method (Maniatis, Molecular Cloning: A Laboratory Manual, Cold Spring Harbor Laboratory Press (1989)). The cells were maintained in culture medium at 37° C., 5% $CO_2$ and diluted 10 fold every 3 days.

The cells were inoculated in 90 mm tissue culture dishes (5×105 cells per flask) in Dulbecco's Modified Essential Medium (DMEM, Gibco BRL), supplemented with 10% fetal bovine serum (FBS), 100 U/ml penicillin, 100 μg/ml streptomycin and 0.25 μg/ml fungizone. One day after inoculation, cells were transiently transfected with 30 μg of plasmid DNA per dish. The cells were harvested 48 hours post transfection for analysis. The expression of the gene was first checked by immunoprecipitation and western blotting with an anti-haemaglutinin antibody. A protein of approximately 43 KD was detected in stably as well as transiently transfected HEK293 cells, but not in control cells.

Stably transfected HEK293 cells were obtained after approximately 21 days of selection in culture medium containing 800 μg/ml G418. Calcium signaling measurement was performed with one of these stably transfected cell line, 293/pcDNA3-HML-HA24. The cells were grown on a 24 mm round glass cover slides to 50–70% confluence. After rinsing the cells with 1.8 NBS buffer (135 mM NaCl, 5 mM KCl, 1.2 mM $MgCl_2$, 1.8 mM $CaCl_2$, 5 mM glucose and 5 mM HEPES, pH 7.3), the cells were incubated for one hour at room temperature in the presence of 0.5 ml of 3.5 µM FURA-2 AM (Molecular Probe, F-1221) diluted in 1.8 NBS. The cells were then rinsed three times with 1.8 NBS and incubated for a further 30 minutes at room temperature. The calcium displacement was measured using a PTI (Photon Technology International) D104 photometer equipped with a PTI Delta RAM High speed multiwavelength illuminator, a PTI SC500 Shutter controller, a PTI LPS220 ARC lamp supply and the PTI FELIX software, v.1.2. Groups of 2 to 8 cells were chosen and isolated with the photometer diaphragm. The cells were exposed to 340 and 380 nm light and the 510 nm light emitted by the cells was recorded. Angiotensin I, II and III, were added successively—in various order from one experiment to the next—followed by bradykinin as a positive control. Upon stimulation with angiotensin II and angiotensin III, a significant response was obtained. Addition of angiotensin I produced no response.

All references cited herein are fully incorporated by reference. Having now fully described the invention, it will be understood by one of skill in the art that the invention may be performed within a wide and equivalent range of conditions, parameters and the like, without affecting the spirit or scope of the invention or any embodiment thereof.

---

The invention claimed is:

1. A substantially pure protein comprising SEQ ID NO:3.
2. The protein of claim 1 wherein the protein consists of SEQ ID NO:3.
3. A composition comprising the protein of claim 1.

* * * * *